US011615687B2

(12) United States Patent
DeMazumder

(10) Patent No.: US 11,615,687 B2
(45) Date of Patent: Mar. 28, 2023

(54) AUTOMATED IDENTIFICATION AND CREATION OF PERSONALIZED KINETIC STATE MODELS OF AN INDIVIDUAL

(71) Applicant: University Of Cincinnati, Cincinnati, OH (US)

(72) Inventor: Deeptankar DeMazumder, Baltimore, MD (US)

(73) Assignee: University Of Cincinnati, Cincinnati, OH (US)

(*) Notice: Subject to any disclaimer, the term of this patent is extended or adjusted under 35 U.S.C. 154(b) by 0 days.

(21) Appl. No.: 16/960,264

(22) PCT Filed: Jan. 28, 2019

(86) PCT No.: PCT/US2019/015426
§ 371 (c)(1),
(2) Date: Jul. 6, 2020

(87) PCT Pub. No.: WO2019/148106
PCT Pub. Date: Aug. 1, 2019

(65) Prior Publication Data
US 2021/0153814 A1 May 27, 2021

(51) Int. Cl.
*G08B 21/04* (2006.01)
*G16H 50/50* (2018.01)
(Continued)

(52) U.S. Cl.
CPC ............. *G08B 21/043* (2013.01); *G06N 3/04* (2013.01); *G06N 3/08* (2013.01); *G08B 21/0453* (2013.01);
(Continued)

(58) Field of Classification Search
CPC ............. G08B 21/043; G08B 21/0453; G08B 21/0476; G16H 50/50; G16H 50/70;
(Continued)

(56) References Cited

U.S. PATENT DOCUMENTS 5,315,285 A 5/1994 Nykerk
6,050,962 A * 4/2000 Kramer ................... G06F 3/011
600/595
(Continued)

FOREIGN PATENT DOCUMENTS

WO 2017040242 A1 3/2017

OTHER PUBLICATIONS

PCT/US19/15426 International Search Report and Written Opinion dated Apr. 11, 2019 by ISA/US.

*Primary Examiner* — John A Tweel, Jr.
(74) *Attorney, Agent, or Firm* — Wood Herron & Evans LLP

(57) ABSTRACT

A system and a method for predicting kinesthetic outcomes from observed position, posture, behavior or activity of an individual 1602, 1702. The system uses kinesthetic activity sensors 102, 104 each collecting one or more of audio, video, or physiological signals and capturing the activity of the individual or an ambient environment of the individual. These signals are delivered into a computer system 106 implementing a learning routine 108 which constructs one or more personalized kinetic state models 1510 of positional states for the individual and transitions between the positional states, and further develops one or more customized multi-dimensional prediction models 1500 for the individual and uses the multidimensional prediction models to predict behaviors, activities and/or positional changes likely to occur in the future, and provides notice of predicted unsafe or undesired outcomes.

48 Claims, 19 Drawing Sheets

(51) Int. Cl.
  *G16H 50/70* (2018.01)
  *G16H 40/67* (2018.01)
  *G16H 50/20* (2018.01)
  *G06N 3/04* (2023.01)
  *G06N 3/08* (2023.01)
  *A61B 5/369* (2021.01)
  *A61B 5/318* (2021.01)
  *A61B 5/00* (2006.01)
  *A61B 5/021* (2006.01)
  *A61B 5/024* (2006.01)
  *A61B 5/08* (2006.01)
  *A61B 5/11* (2006.01)
  *A61B 5/1455* (2006.01)

(52) U.S. Cl.
  CPC ......... *G08B 21/0476* (2013.01); *G16H 40/67* (2018.01); *G16H 50/20* (2018.01); *G16H 50/50* (2018.01); *G16H 50/70* (2018.01); *A61B 5/0077* (2013.01); *A61B 5/021* (2013.01); *A61B 5/02405* (2013.01); *A61B 5/08* (2013.01); *A61B 5/1113* (2013.01); *A61B 5/14551* (2013.01); *A61B 5/318* (2021.01); *A61B 5/369* (2021.01); *A61B 5/4806* (2013.01); *A61B 5/4866* (2013.01); *A61B 2560/0242* (2013.01); *A61B 2560/0431* (2013.01); *A61B 2560/0475* (2013.01); *A61B 2562/0204* (2013.01); *A61B 2562/0219* (2013.01)

(58) Field of Classification Search
  CPC .......... A61B 2562/0219; A61B 5/1114; A61B 5/1116; A61B 5/1117; A61B 5/1118; A61B 5/1123
  See application file for complete search history.

(56) References Cited

U.S. PATENT DOCUMENTS

| | | | |
|---|---|---|---|
| 6,922,585 | B2 | 7/2005 | Zhou et al. |
| 8,684,922 | B2 * | 4/2014 | Tran ...................... G09B 19/00 600/300 |
| 10,854,104 | B2 * | 12/2020 | Mettler May .......... A61B 5/742 |
| 2013/0191161 | A1 | 7/2013 | Churchwell et al. |
| 2015/0026061 | A1 | 1/2015 | Siegel et al. |
| 2015/0164437 | A1 | 6/2015 | McCombie et al. |
| 2015/0310173 | A1 | 10/2015 | Coney |
| 2016/0199215 | A1 | 7/2016 | Kopelman |
| 2017/0055896 | A1 | 3/2017 | Al-Ali et al. |
| 2017/0173262 | A1 | 6/2017 | Veltz |

* cited by examiner

AUTOMATED IDENTIFICATION AND CREATION OF PERSONALIZED KINETIC STATE MODELS OF AN INDIVIDUAL

STATEMENT REGARDING FEDERALLY SPONSORED RESEARCH OR DEVELOPMENT

The present invention was made, at least in part, with support from the U.S. Government and funds identified as NHLBI K99 HL 130662 and NHLBI R00 HK 130662 awarded by the National Institute for Health. The U.S. Government has certain rights in the present invention.

CROSS-REFERENCE TO RELATED APPLICATIONS

The present invention is a U.S. National Patent Application to PCT Application No. US2019/015426 filed Jan. 28, 2019, which claims priority to U.S. Provisional Application Ser. No. 62/622,171 filed Jan. 26, 2018 and U.S. Provisional Application Ser. No. 62/622,989 filed Jan. 29, 2018, all of which are incorporated herein in their entirety.

BACKGROUND OF THE INVENTION

In several custodial environments, monitoring of persons is critical to avoid unsafe or undesirable situations. Examples include hospital and hospice environments, childcare centers, zoos and animal/pet care centers, secure facilities of governmental offices, secure areas open to the public such as airports, ports of entry and museums, prisons, police stations and other law enforcement areas, markets and other public shopping centers, casinos, entertainment venues, and other areas open to the public.

To provide security and safety in these environments, security cameras are typically installed in selected locations to monitor the movements and activity of persons and/or animals so that a security guard at a monitoring station can observe activities and identify potentially hazardous activities or persons and identify developing situations and marshal assistance as needed. This approach relies upon human intuition of normal and abnormal behaviors and movement patterns and relies upon the vigilance of the security guard or guards at monitoring stations. In some cases, activity is recorded by cameras for later review, but is not actively monitored.

As in many other circumstances, early detection or prediction of an unsafe or undesirable situation is critical to avoid or ameliorate the effects of that situation. Recording with security cameras cannot accomplish predictive or prophylactic goals. Human monitoring by security guards can in some cases predict future problems but is limited by the vigilance of the guard, their understanding of behaviors and familiarity with the individuals and conventional movements of those individuals, and often cannot accomplish much more than to summon help after a problem has occurred.

One specific example where these challenges arise is in the monitoring of patient rooms, particularly in hospitals and nursing or hospice facilities, where infirm or debilitated patients often fall and are injured when moving in a hospital room or about a hospital suite. Current monitoring strategies have proven inadequate, leading to an estimated one million preventable hospital falls each year in the United States, approximately one-third of which result in an injury and an estimated $34 billion of additional hospital expense caused by extended hospitalization and treatment for fall-related injuries. The key factor for preventing these injuries is providing monitoring that allows for enough lead time for healthcare caregivers (nurses, etc.) to identify an unstable patent situation and respond to it before there is a fall and injury.

Similar situations and needs arise in the other environments identified. For example, in childcare centers, behaviors likely to lead to child injuries need to be identified and addressed before they lead to injury. In zoos or animal/pet care centers, animal behaviors or human/animal interactions need to be evaluated continuously to predict when an unsafe situation may occur, such as the recent event in the Cincinnati Zoo where a child entered a gorilla paddock leading to a life-threatening situation and the death of a gorilla at the hands of the zookeepers. In a secure government facility or secure area, or any market, shopping or entertainment venue open to the public, the activities of persons need to be monitored for behaviors suggesting violent intent, unauthorized access to facilities, or harassment of patrons, ideally leading to a response before harm comes to persons or property at that location.

Effective continuous monitoring of these environments can uniquely improve outcomes by predicting unsafe or undesirable situations and impending adverse and respond to them before harm to persons or property and can save many lives.

SUMMARY OF THE INVENTION

The present invention provides, broadly, a system and a method for predicting kinesthetic outcomes from observed position, posture, behavior or activity of an individual. The system uses kinesthetic activity sensors each collecting one or more of audio, video, or physiological signals and capturing the activity of the individual or an ambient environment of the individual. These signals are delivered into a computer system implementing a learning routine which constructs one or more personalized kinetic state models of positional states for the individual and transitions between the positional states, and further develops one or more customized multi-dimensional prediction models for the individual, and uses the multi-dimensional prediction models to predict behaviors, activities and/or positional changes likely to occur in the future. The system further includes a notification system initiating a notification, alert or warning upon prediction of a behavior, activity or positional change associated with an unsafe or undesired outcome, and transmitting the notification, alert or warning to a recipient associated with the individual.

In detailed particular embodiments, the recipient associated with the individual is one or more of a custodian or caretaker for the individual, a coach or trainer for the individual, and a storage system for storing notifications, alerts or warnings. Thus the system may be applied not only to custodial or caretaking environments but also to coaching and training.

In a hospital, clinical, ambulatory or home environment, the system may predict falls or other injury situations, by notifying a caretaker of the likelihood of a fall by the individual. For such environments, the data collected from the kinesthetic activity sensors can be secured in a manner compliant with applicable rules and regulations of patient confidentiality. In such environments, a large number of physiological signals may be available to improve the modelling, including but not limited to changes in electrocardiography, respiration, temperature, blood pressure, saturation of blood oxygen, intracardiac pressures, electroencephalogram and positional signals.

In detailed embodiments, the system may be responsive to ambient environmental sources include but are not limited to haptic, accelerometric, gyroscopic, temperature, visual, auditory or positional changes of objects in the immediate vicinity of the individual, and the kinesthetic activity sensors may detect audio signals of all sound spectrums including but not limited to the frequencies of human hearing, and may capture video or images of visible, infrared, thermal and/or ultraviolet light. Sensors can capture data from a plurality of locations having visibility of the individual, so that the learning routine can identify the position of key positional points for the individual in a three-dimensional Cartesian plane using a combination of video or images acquired from said plurality of locations. Further, the kinesthetic activity sensors may capture haptic, tactile, pressure, accelerometric, gyroscopic and/or temperature data from the vicinity of the individual.

According to principles of the present invention, the system may detect behavior, activity or a positional change associated with an unsafe or undesired outcome such as an unsteady gait of the individual or proximity of the individual to a harmful object.

In the particular embodiment described below, the learning routine comprises one or more of a supervised routine comprising linear and logistic regression, support vector machine, naive Bayes, neural network, gradient boosting, classification trees and random forest, and an unsupervised routine comprising K-means, hierarchical clustering or mixture models, dimensionality reduction, anomaly detections, reinforcement learning, or another feedback-based method. These can be implemented using a deep structured learning, neural network.

In a hospital environment, the learning routine can be further responsive to data relating to the individual from electronic health or medical records, and may also use sensor data from a wearable device.

The present invention anticipates that the learning routine collects multi-dimensional data for more than one individual, and discerns the presence of different individuals using data from electronic health records and/or data from wearable devices. An individual can be identified and then the system can develop a personalized kinetic state model for the individual characterizing the behavior, preferred positions, preferred movement and rate of change in positions or movement of that individual.

The kinds of positional states of the individual that could be identified include sleeping, supine, sitting, getting up from a bed or chair, standing, ambulating, walking, unsteady gait, exercising, eating, transition states, and the same types of states could be predicted and identified as unsafe or unsound for a particular individual model, depending upon the current state and events of predictive value of later behaviors, activities and/or positional changes, such as delivery of food (which may predict sitting up); administration of sedatives (which may predict sleeping); time since last bathroom visit (which may predict sitting up); change in heart rate, respiration, pulse oximetry and/or electroencephalogram (which may predict upcoming motion). These predictions can be responsive to recurring behavior and personal habits of the individual based on one or more of: time of day and degree of recurrence and length of time spent in distinct postures, positions, behaviors or activities.

Kinesthetic models can utilize pooled data of similar individuals to develop an initial kinesthetic state model and starting conditions therefor, for subsequent personalization to the individual, so that personalization comprises one or more of adding states, subtracting states, ordering states, and developing rate constants for transition into and out of states, and/or adjustment of the number and description of and adjustment of rate constants and coefficients characterizing state transitions, based upon the match of predicted and actual changes in the individual's posture, position, behavior or activity.

As described herein, the learning routine defines a plurality of states, s, and characterizes each state by the amount or percent of time, t, spent therein and the degree of recurrence, r, of a certain position, posture, behavior or activity. The learning routine then further defines one or more boundary conditions for distinguishing an individual from environmental objects or other individuals, and the learning routine re-evaluates previously designated states and adds or subtracts states, adjusts boundary conditions, and modifies transition rates and other coefficients to create one or more dynamic personalized kinetic state models based on t, r, and total duration of observation for an individual.

In the described particular embodiments, the personalized kinetic state models measure rates of transition between one or more states and determine the rate constants for transition into or out of each state with respect to time, with rate constants described by coupled differential equations. The learning routine comprises full or partial numerical integration of the coupled differential equations to predict transitions between states based on temporal sequence and occupancy of one or more states. The personalized kinetic state models include coefficient values which weigh the rates of transitions into, occupancy probabilities of and confidence intervals of entering each state, and behaviors, activities and/or position changes are predicted by prospectively comparing the actual vs. predicted occupancies of said state and the time to occupancy of said state. The learning routine uses the personalized kinetic state models to calculate likelihood, hazards ratio, confidence intervals, conditional probabilities of entering a certain state given the occupancy of one or more other states within a certain temporal period or volume space, and an nth-order probability density function for the ordered sequence of states, rates of transition to and from one or more states, and feedback weighing of these factors and coefficients based on the positive and negative predictive accuracy of each model.

Consistent with principles of the present invention, the learning routine is responsive to data from electronic health or medical records and physiological signals to assess predictive accuracy of the personalized kinetic state model and modify the kinetic state model based thereon. For example, the learning routine uses heart rate and electroencephalogram characteristics indicating an individual is sleeping to evaluate probability of transition to a state of standing posture, and the learning routine uses heart rate and electroencephalogram characteristics indicating an individual is sleep walking to evaluate the probability of transition to a state of standing posture.

The one particular embodiment, the personalized kinetic state model may comprise a plurality of dynamic kinetic models for the same individual, the dynamic kinetic models applicable to specific time scales, thermodynamic energetics, or volume spaces. In this case, the learning routine utilizes interactions between multiple dynamic kinetic models at multiple time scales, thermodynamic energetics, or volume spaces for the individual to create multi-dimensional prediction models for the individual.

The present invention contemplates that the system produces a notification, alert or warning directed to one or more of deploying a safety system or advising of a necessary action to relevant personnel. The relevant personnel may be law enforcement, emergency workers, or health care providers, or nearest available trained personnel.

In particular embodiments, the notification, alert or warning comprises the individual's predicted state and location, such as a room number, longitude/latitude, elevation, and triangulation information. Further, the notification, alert or warning may comprise one or more of audio and/or video instruction to the individual, or a custodial person, and may also comprise a deployment of counter measures such as fall-prevention devices.

The system may utilize a storage device for storing data upon detection of an individual engaged in or predicted to be in an undesired or unsafe position, posture, behavior or activity; this storage may be a database or electronic record comprising electronic medical records, wherein the computer system updates work flow into the medical records programs. The storage system may employ an encryption algorithm to securely record and store kinesthetic activity sensor data to limit the use of the same to personnel or officials with approved clearance thereto.

The computer system that implements the invention may comprise one or more computers, servers, microprocessors, electronics platforms, processing devices, mobile computing devices, or other electronic hardware, software, wireless and sensory devices; depending upon the devices and equipment used, the invention may provide a relatively inexpensive solution to the challenge of monitoring or reviewing persons and locations that is cost-competitive with the use of human supervision and potentially provides higher quality results.

The above and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION OF THE INVENTION

Hardware Environment

The present invention will be elaborated with reference to a specific embodiment applied to a hospital room suite and monitoring station for that suite. While this environment will be described in some detail, the principles of the invention are applicable to numerous other environments and circumstances as noted herein.

Figure 1:
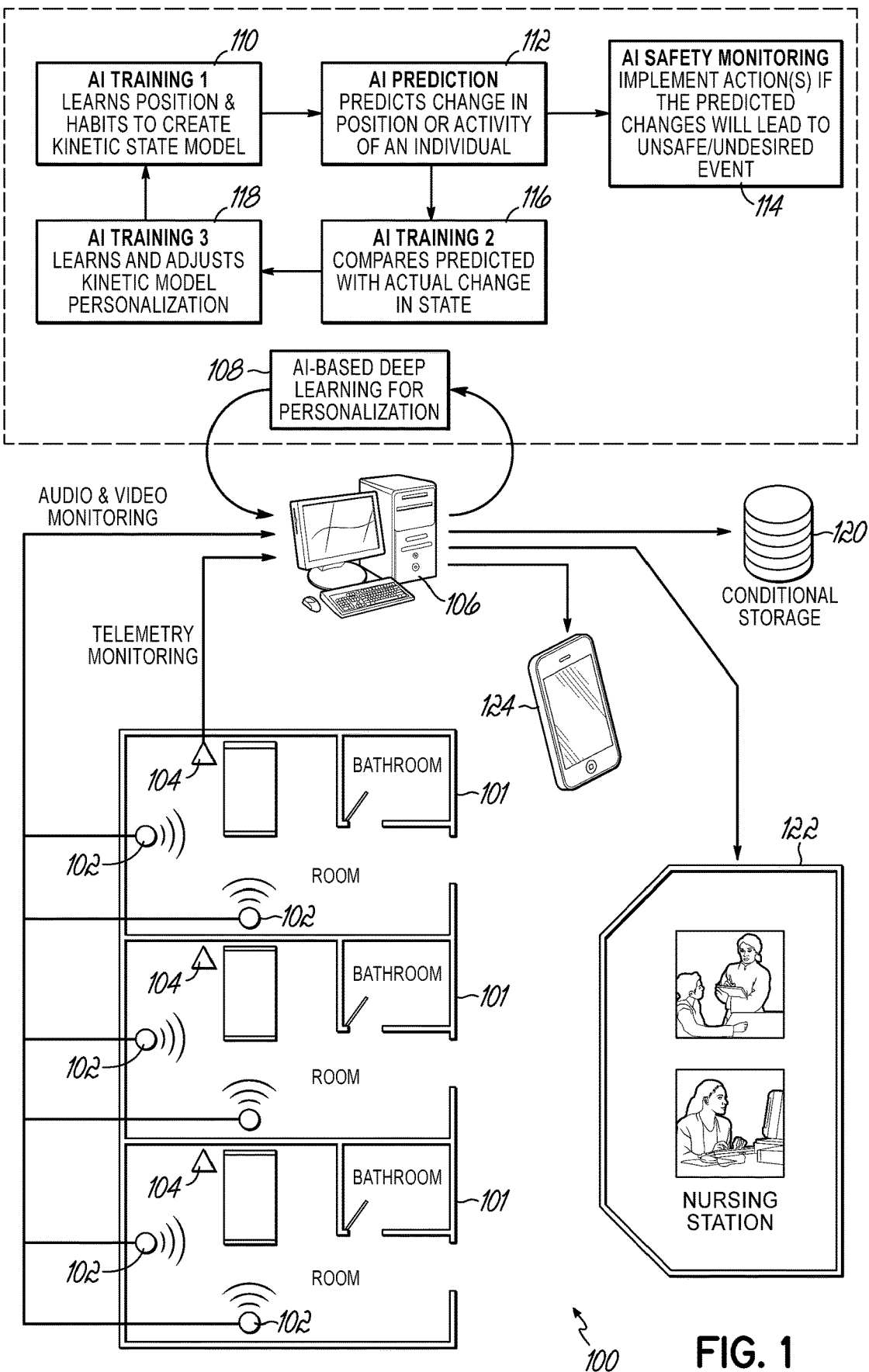
FIG. 1 is a simplified schematic example of personalized AI-based monitoring for early prediction and prevention of an unsafe or undesired position, posture, behavior or activity (e.g., patient fall in a hospital setting)

Referring now to FIG. 1, a system according to the present invention applied to a hospital environment 100 uses video and audio monitoring devices 102 and acceleration/telemetry measuring devices 104 in each patient room 101 to monitor, and then learn and predict the behavior, positional change and activity in individuals in each patient room 101.

The system performs this observation and learning using a workstation, server or server farm 106 which is coupled to each monitoring device 102, 104 and implements an artificial intelligence based deep learning routine 108 for personalizing behavioral models for each individual being observed.

As seen in FIG. 1, the deep learning routine comprises an initial AI training routine 110 in which the system collects multi-dimensional data of position and movement of a subject and learns habits/"body language" of that subject by forming a kinetic state model using a multi-dimensional version of the state modeling methods described below.

Thereafter, in step 112, the developed multi-dimensional model is utilized to predict forthcoming changes in position or activities of an individual. These predictions may then be used in step 114 to implement responsive actions if the predicted changes in position or activity will lead to an unsafe or undesired event. For example, if a patient who has been ordered not to get out of bed begins sitting up to get out of bed, an appropriate responsive action would be triggered. Similarly, a patient observed to be staggering or walking unsteadily would trigger an appropriate responsive action.

Actions triggered in step 114 may be implemented in a number of outputs. Initially, any observed conditions or situations may be written to a conditional storage database 120 for later retrieval, audit, and evaluation of both patient activity and the accuracy of the predictions generated by the deep learning routine 108. Furthermore, depending upon the severity of a condition or situation, notice thereof may be delivered to a supervisory station 122 (e.g., nursing station) occupied by live personnel who may intervene and ameliorate a dangerous or undesirable activity or movement. In addition, notifications may be delivered to notification devices 124, such as a smartphone associated with the individual under monitoring or family members or other persons nearby. Notification devices may also be permanently positioned within rooms 101 to deliver direct feedback to an individual (e.g., a responsive verbal warning like "do not get out of bed, your sedation has not yet worn off").

The deep learning routine 108 implemented by system 100 seen in FIG. 1 uses an iterative process to progressively increase its predictive accuracy for each individual under monitoring. This is accomplished in step 116 where the predicted movements or activities of an individual are compared with actual changes in state of that individual, so that in step 118 the difference may be used to learn and adjust the kinetic model for the individual and create greater personalization for that individual.

The principles of the present invention underlying the deep learning routine 108 of the system 100 of FIG. 1 will now be described by way of the description of mathematical concepts and equations which can underlie the automated development and improvement of a multi-dimensional personalized kinetic state model of an individual's position, behavior and/or activity.

GENERAL CONSIDERATIONS

The following discussion applies ideas and concepts from chemical kinetics to construct a kinetic model of human (or animal) positions, movement and behavior that continues to tailor itself to an individual over the course of analysis using artificial intelligence (AI). Some additional concepts must be included to study the kinetics of human or animal states as chemical reactions were not designed to be studied at the resolution of a single organism. These additional concepts come from the mathematics of probability.

In the simplest case, the underlying assumption is that a simple Markov process governs a "transitional gate", which allows a person to go from one position/action to another. At the onset of analysis, this transitional change may be a relatively big change, such as going from standing to sitting position. With continued recordings and analysis, this transitional change be much smaller movements, such as movement of the pupils in the eye, movement of a finger, etc. Based on Markovian theory, the probability that the positional change occurs is constant in time and that the probability depends only on the present positional state of the person, not on the state of this position at earlier times. While the AI-based analyses will ultimately consider the sequence of prior state occupancies, the initial simplest assumption for initial model creation is that the transition gates have no memory of what has occurred in the past.

We will consider three types of analyses. Macroscopic analyses will be applied on positional and movement data obtained via different types of recording modalities (e.g., audio/video, accelerometry, gyroscope), and those obtained via the same modality but from different body regions (e.g., hand, foot, head), forming an ensemble of many changes of various body regions in an individual. Microscopic analyses will be applied for the study of fewer body regions, typically just one body region (e.g., left shoulder). In addition to body positional and movement data, other body signals (e.g., electrocardiogram, photoplethysmogram, electroencephalogram) or environmental monitoring signals (e.g., temperature, sound) will be analyzed to supplement the macroscopic and microscopic analyses.

We will also refer to steady-state (equilibrium) analyses and kinetic analyses. The steady-state tells us, for a given set of conditions, the probability of occupancy of each state in the constructed Markov model after a certain period of time. The kinetics tell us, for a given starting condition (supine position in a certain location), how long will it take to reach the steady-state (standing position in another location).

Steady-state equations can be obtained using algebra. Kinetic equations require the use of calculus (differential equations). Only the simplest models can be solved analytically, that is, the answer can be expressed in the form of an equation that can be solved with a calculator. The other models require the use of numerical analysis. High performance computing may be needed depending on a number of factors, such as the quality of recording (e.g., resolution, number of bits for digitization, sampling rate), total number of 3-D body regions in concurrent macroscopic analysis for model creation, and total number of concurrent microscopic analyses being performed. This is because each time a parameter changes in the system, the computer has to start calculating again from the beginning to come up with the probability estimate of occupying a certain state within a certain period of time. Additionally, creation of personalized models requires the use of A to learn individualized characteristics and patterns in multi-dimensional analyses (e.g., temporal, frequency and nonlinear domains) of position, movement and other body signals.

Initial 2-State Model

The simplest model to consider for changes in position of a body region is a 2-state model. For the purposes of example and not to be intended to be limiting in any way, the analyses of a finger (microscopic) and the whole hand (macroscopic) will be described to illustrate the steps used by the program to construct a model. The same steps are used to construct models for different regions of the body that are integrated by AI to form the primary model.

In this example, consider that a person is repetitively opening and closing his fingers such that a hand can exist in only one of two states: closed and open. The initial 2-state model analysis of movement along a single dimension (e.g., x axis) can be further refined by incorporating data from all 3 dimensions (x, y, z axes) and incorporated into a multi-state model (e.g., each state representing the multi-dimensional position of each finger). The following diagram of a 2-state model represents the closed and open position of a person's hand in a single vector space:

Model 1

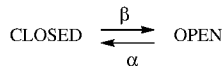

The process of going from one state to another is called a transition. The transition rate, α and β for this two-state model, is the rate at which the fingers open (β) and close (α). The rates are measured in transitions per second. If the opening rate is 1 per second, then the finger spends an average of 1 second (1 divided by rate) in the closed state before entering the open state. If the closing rate is 10 per second, then each finger spends an average of 0.1 seconds in the open state before entering the closed state.

The first thing the computer program will calculate is the steady-state number of open fingers within a certain period of time (e.g., 90% open). To do this, we use the definition of steady-state: at the steady-state, the number of fingers opening in 1 second, is equal to the number of fingers closing in 1 second. To get the number of fingers opening in 1 second, multiply the number of closed fingers ($N_c$) by the opening rate (β). To get the number of fingers closing in 1 second, multiply the number of open fingers ($N_o$) by the closing rate (α).

$$N_c \times \beta = N_o \times \alpha \qquad \text{Eq. 1}$$

The sum of $N_c$ and $N_o$ is the total number of fingers, $N_t$. The fraction of open fingers is $N_o/N_t$. Using algebra, we can solve for the fraction of open fingers as a function of just the transition rates:

$$\frac{N_o}{N_t} = \frac{\beta}{\alpha + \beta} \qquad \text{Eq. 2}$$

The fraction of open fingers increases when the opening rate (β) increases and decreases when the closing rate (α) increases. Here are a few examples of the numerical results:

| β (1/s) | α (1/s) | $N_o/N_t$ |
|---|---|---|
| 0.1 | 1 | 0.1 ÷ 1.1 = 0.091 |
| 0.5 | 1 | 0.5 ÷ 1.5 = 0.33 |
| 1 | 1 | 1 ÷ 2 = 0.50 |
| 2 | 1 | 2 ÷ 3 = 0.67 |
| 9 | 1 | 9 ÷ 10 = 0.90 |

The next question the computer program asks about Model 1 has to do with the kinetics. If the system is perturbed so that it is no longer in its steady-state condition, how long does it take to reach a new steady-state? Here's where the calculus comes in. The computer program sets up a differential equation that describes how the number of closed fingers changes during a small time step. This equation is constructed as follows: The number of fingers leaving the closed state will be a product of the number of fingers occupying the closed state multiplied by the transition rate constant from closed to open state. Similarly, the number of fingers entering the closed state will be a product of the number of fingers occupying the open state multiplied by transition rate constant from open to closed state. In mathematical terms, this equation is:

$$\frac{dN_c}{dt} = -\beta N_c + \alpha N_o \qquad \text{Eq. 3}$$

Eq. 3 says that, during a small time step (dt), the number of closed fingers will decrease because some closed fingers will open ($-\beta\, N_c$) and will increase because some open fingers will close ($\alpha\, N_o$). The sum of these two factors determines the net change in the number of closed fingers.

A similar equation can be written for the number of open fingers.

$$\frac{dN_o}{dt} = \beta N_C - \alpha N_O \qquad \text{Eq. 4}$$

The idea is to find expressions for $N_c$ as a function of time, $N_c(t)$, and $N_o$ as a function of time, $N_o(t)$, that solve equations 3 and 4. The key to the solution is that the derivative of an exponential function is equal to a constant times the exponential (exp) function:

$$\frac{d}{dt}\exp(at) = a\exp(at) \qquad \text{Eq. 5}$$

The solutions are in the following form $$N_c = N_{c1}\exp(-\lambda t) + N_{c2} \qquad \text{Eq. 6}$$

$$N_o = N_{o1}\exp(-\lambda t) + N_{o2} \qquad \text{Eq. 7}$$

where there are 5 constants that must still be evaluated: $N_{c1}$, $N_{c2}$, $N_{o1}$ and $N_{o2}$ are amplitude constants and λ is the rate constant.

The amplitude constants are evaluated from the initial conditions (the number of closed and open fingers at time zero, using exp(0)=1):

$$N_c(0) = N_{c1} + N_{c2} \qquad \text{Eq. 8}$$

$$N_o(0) = N_{o1} + N_{o2} \qquad \text{Eq. 9}$$

and the steady-state values (using exp(∞)=0):

$$N_c(\infty) = \frac{\alpha}{\alpha + \beta} = N_{c2} \qquad \text{Eq. 10}$$

$$N_o(\infty) = \frac{\beta}{\alpha + \beta} = N_{o2} \qquad \text{Eq. 11}$$

The rate constant is evaluated by differentiating Eqs. 6, 7, substituting into Eqs. 3, 4 and grouping the exp terms together (using algebra).

$$\lambda = \alpha + \beta \qquad \text{Eq. 12}$$

This tells us that the distribution of closed and open fingers reaches a new steady state at a rate equal to the sum of the opening and closing rate constants. Another way to express this is to say that the time constant (τ) for the system (the reciprocal of the rate constant) is equal to 1/(α+β). Here are examples of some numerical results:

| β (1/s) | α (1/s) | τ (s) |
|---|---|---|
| 0.1 | 1 | 0.91 |
| 0.5 | 1 | 0.67 |

-continued

| β (1/s) | α (1/s) | τ (s) |
|---------|---------|-------|
| 1 | 1 | 0.50 |
| 2 | 1 | 0.33 |
| 9 | 1 | 0.090 |

The time constant depends on both the opening and closing rates. When one rate is much faster than the other, the faster of the two rates is the more important one.

Next, the program puts together all of the macroscopic results for the 2-state model to find out how the number of open and closed fingers changes with time. Let's assume that at time zero all of the fingers are in the closed state. Also, because this will be a probability calculation, the total number considered will be 100, representing 100% of the hand comprised by the five fingers. In this way, any number of similar parts of a body region may be considered together.

Figure 2A:
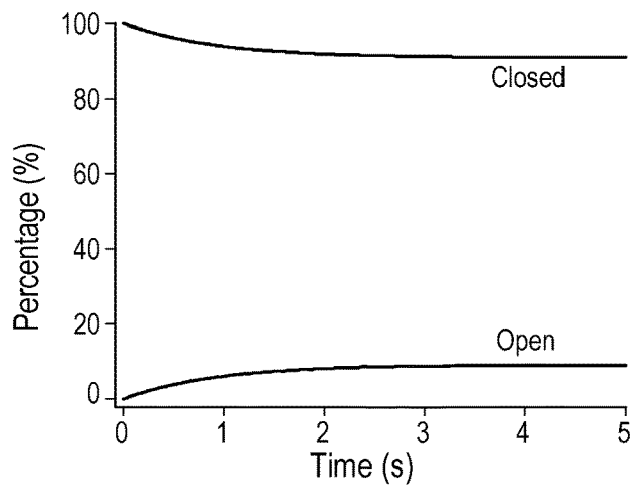
FIGS. 2A, 2B and 2C are graphs of a 2-state model, where the states represent open and closed states of a human hand, illustrating the percentage of open and closed fingers under steady-state conditions as a function of time.
Figure 2B:
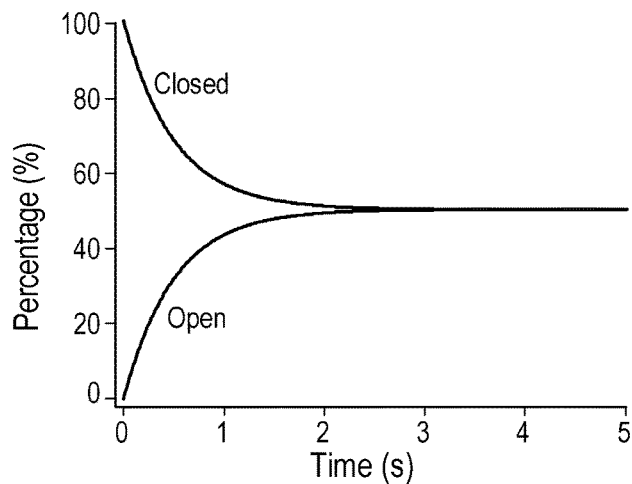
Figure 2C:
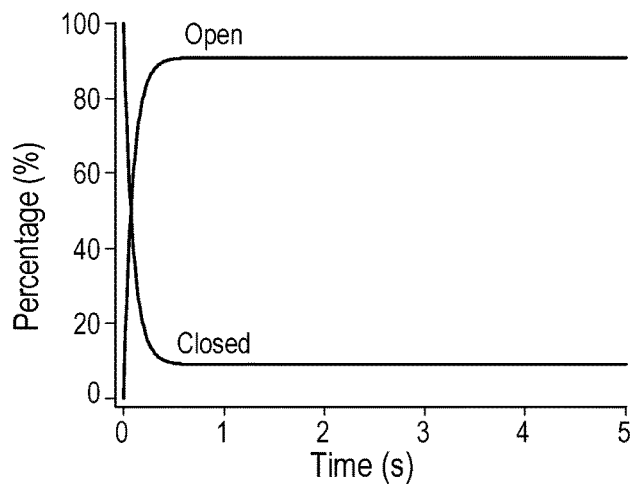

FIGS. 2A, 2B and 2C show the time dependence of the percentage of time for each possible condition where: in FIG. 2A the rate of finger opening is slow compared to finger closing: $\beta=0.1/s$, $\alpha=1/s$; in FIG. 2B finger opening is the same speed as closing: $\beta=1/s$, $\alpha=1/s$; in FIG. 2C finger opening is fast compared to closing: $\beta=10/s$, $\alpha=1/s$.

Next, consider how this 2-state model behaves when the program analyzes data in a single vector field from only one finger. The expression for the fraction of open fingers $N_o/N_t=\beta/(\alpha+\beta)$ (Eq. 2) takes a new meaning when only one finger is present. It becomes the average fraction of time that this finger is open. If the opening and closing rates are the same ($\beta=\alpha=1$), then the finger is open one-half of the time on the average. But we can be more precise about how the finger divides its time between the closed and open states. The average open time, $\tau_o$, depends only on the closing rate $\tau_o=1/\alpha$. The average closed time, $\tau_c$, depends only on the opening rate $\tau_c=1/\beta$. With ($\beta=\alpha=1$), $\tau_o=\tau_c=1$ s. Here are some examples of these other numerical results:

| Finger | β (1/s) | α (1/s) | $\tau_c$ (s) | $\tau_o$ (s) |
|--------|---------|---------|--------------|--------------|
| 1 | 0.1 | 1 | 10 | 1.0 |
| 2 | 0.5 | 1 | 2.0 | 1.0 |
| 3 | 1 | 1 | 1.0 | 1.0 |
| 4 | 2 | 1 | 0.50 | 1.0 |
| 5 | 10 | 1 | 0.10 | 1.0 |

Figure 3:
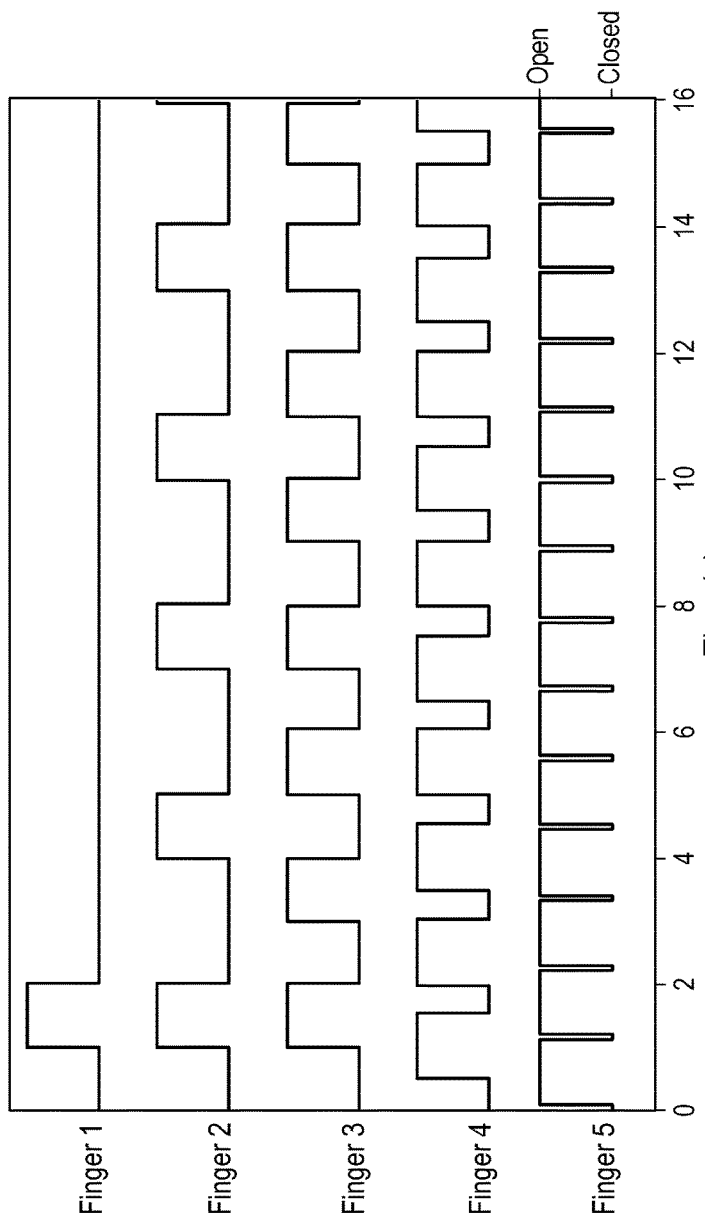
FIG. 3 is a time sequence representation of the average behavior of a finger described by the two-state model.

For the data from five fingers (1-5) of a hand listed above, the average single finger events (closed or open) in a single vector space (i.e., x-axis) are shown in FIG. 3. In the traces 1 $\beta=0.1$, $\alpha=1/s$; trace 2 $\beta=0.5$, $\alpha=1/s$; trace 3 $\beta=1$, $\alpha=1/s$; trace 4 $\beta=2$, $\alpha=1/s$; trace 5 $\beta=10$, $\alpha=1/s$.

In these examples, the closing rate is the same, so the average open time is always 1 s. As the opening rate increases from 0.1/s to 10/s, the average closed time decreases, and the finger spends more of its time in the open state. Each panel of FIG. 3 shows all of the open times (and closed times) equal to the average value. As in any real measurements, there will be variations in the open times. The variation may be large in the case of a single finger's movement in a single dimension (x-axis), which only partially captures the full movement. However, this initial 2-state model in a single vector space considers the process of the finger moving from open to closed positions to be occurring as random events.

The program also applies the same method described above for the open times to the closed times.

Figure 4:
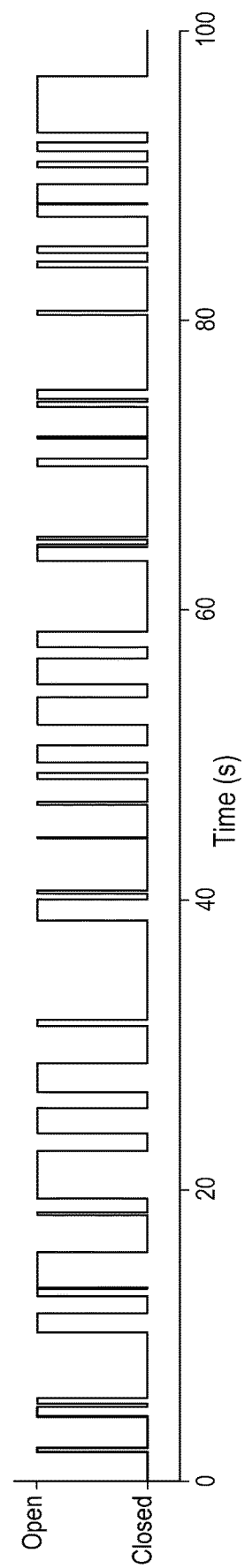
FIG. 4 is a time sequence representation of a finger's activity when openings and closing are considered to be random events in a 2-state model and FIG. 5 is a histogram of the distribution of finger open times based on the data in FIG. 4.

FIG. 4 shows a more realistic display of a finger's activity ($\beta=0.5$, $\alpha=1/s$; Finger #2 in FIG. 3). There are 37 openings. The average fraction of time that the finger is in the open state is 0.34 (the model's predicted value is 0.33). The average open time is 0.92 s (the model's predicted value is 1.0 s).

Figure 5:
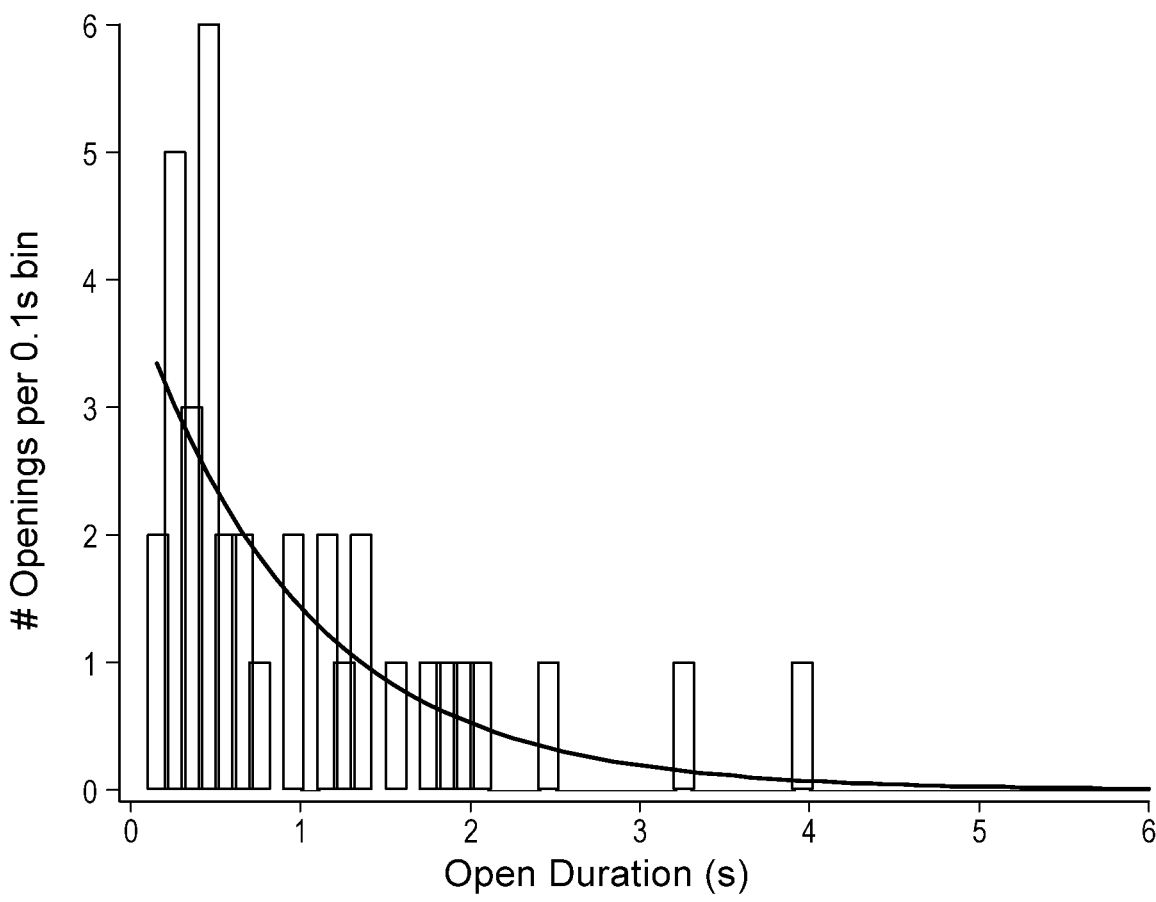

A histogram of the distribution of time spent in the open state is shown in FIG. 5. The smooth curve represents the predicted distribution. The range of open times is quite large (0.05-3.8 s). The variation is also evident from the large standard deviation of the open times (1.2 s). The assumption that process of finger closing is a random event is what gives rise to this large variation in open time.

Radioactive decay is also considered to be a random process. The "half-life" for a radioactive isotope is very close to the average lifetime of each radioactive atom in a sample. For example, the half-life for radium-226 is 1600 years. However, a Geiger counter will attest that some of the atoms in a sample containing this isotope are decaying at any given measurement time. Many others will not decay for thousands of years. The variation for this random process is huge, but the average lifetime information accurately characterizes critical information about an isotope, forming the basis for countless critical projects. In comparison, the variation of the average opening and closing times of a finger is far less, and contributes important insight for constructing a kinetic model, starting with the hand and extended to numerous points of motion throughout the whole body, and tailored to an individual's behavior and characteristics.

Figure 6A:
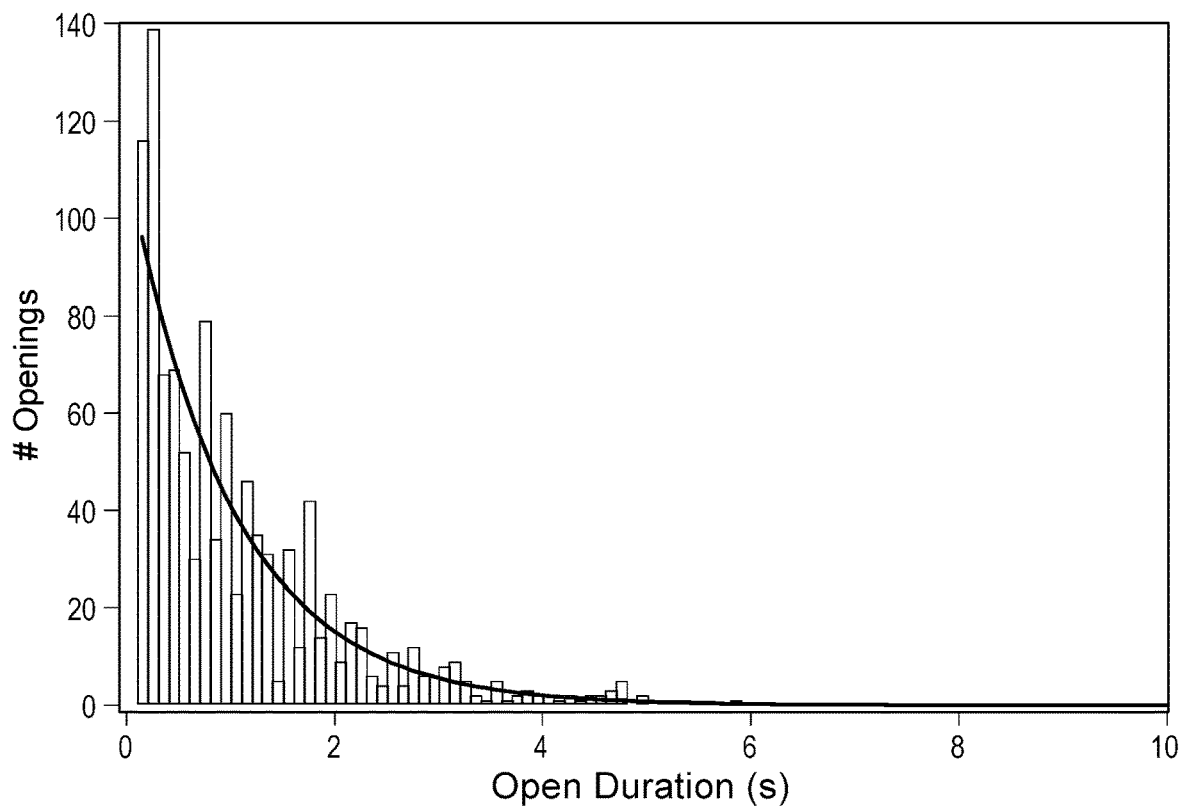
FIG. 6A is a histogram of a distribution of finger open times.

The predicted shape of the open time histogram over a long period is an exponential distribution (i.e., the smooth curve in FIG. 6A shows this prediction for the 2-state model with a mean open time of 1 s). The computer program studies all related body parts in the region (i.e., all the fingers in the hand) in order to judge how closely the observed distribution fits the predicted distribution. Depending on application purpose, the 2-state model can approximate the behavior of a more complicated system. For example, the "thumbs up" and "closed fist" positions can be collapsed into a single closed state or modeled as distinct states in a more complicated model (as discussed later on in this application). Because the open and closed times of single finger events are broadly distributed, it is usually more convenient to view them on a logarithmic time scale, as seen in FIG. 6B.

Figure 6B:
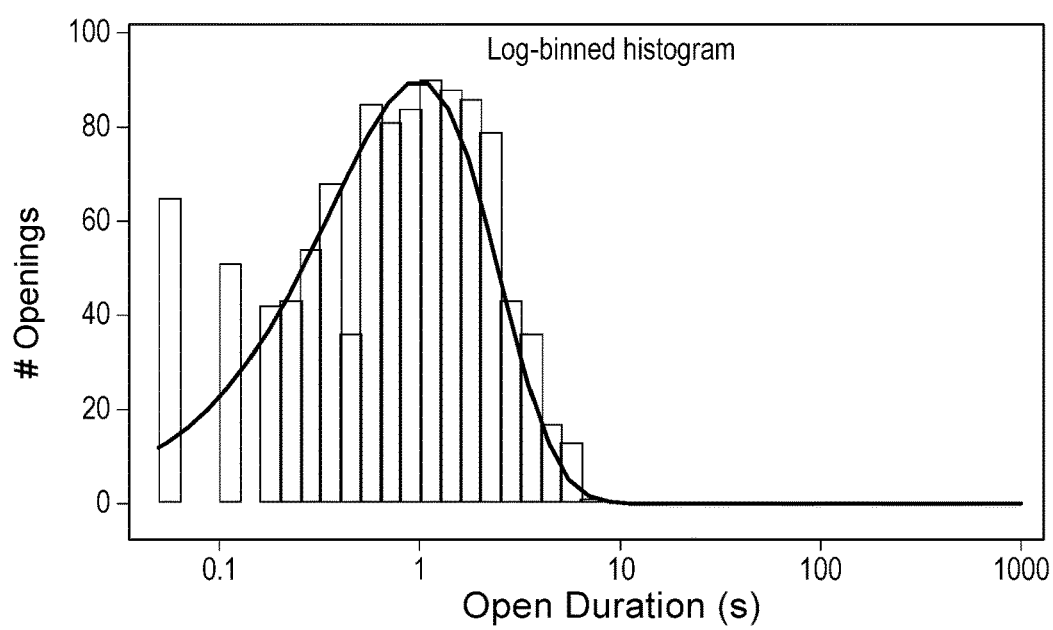
FIG. 6B illustrates the open times of FIG. 5A in a log-binned histogram.

Referring to FIG. 6B, compared to a linear histogram, a log-binned histogram provides a better view of the wide range of event durations, as evident in this example of >1000 events. Further, the log-binned histogram reveals additional features: (1) the peak of the distribution corresponds to the mean open (or closed) time; (2) the number of peaks in the distribution corresponds to the number of exponential functions needed to describe the distribution. The number of peaks is used by the computer program to judge how many states are needed to accurately describe the distinct characteristics.

To summarize the above, the 2-state (closed/open) Markov model of a hand makes several predictions about the single finger and macroscopic hand behavior. Specifically, for analysis of single finger movement:

The open and closed time distributions are described by single exponential functions.

The mean open time is equal to the reciprocal of the closing rate ($1/\alpha$).

The mean closed time is equal to the reciprocal of the opening rate ($1/\beta$).

More complicated kinetic models that are better described with additional states For a whole hand (macroscopic):

The fraction of open fingers at equilibrium is given by:

$$\beta/(\alpha+\beta) \quad \text{Eq. 5}$$

After a perturbation, a new equilibrium is reached with an exponential time course with a time constant of $1/(\alpha+\beta)$.

Note that the macroscopic equations depend on both open and closed rate constants. Also, both macroscopic and single finger equations contain the same information about the kinetic model. In practice, the information may be more easily obtained with one type of measurement, but the computer program considers both types of measurements and checks the results for internal consistency. Two assumptions are needed to translate results of single finger analysis to macroscopic analysis.

In an ensemble of finger analysis, the fingers are "identical". Methods such as variance ratio analysis of the data can be used to test this assumption.

The fingers do not interact with each other. Rather, they act independently. This assumption can be tested using various methods for collinear and principle component analyses to assess where there are interactions between the designated microscopic components. This allows for grouping of regional body parts for microscopic and macroscopic analysis.

A computer program may assess different groups of body regions in parallel to select body regions for analysis when both assumptions are true. If tested true, then the behavior of macroscopic models can be predicted from that of the microscopic model simply by adding up (superimposing) many microscopic events (e.g., single finger events). A few examples are shown in FIGS. 7A, 7B and 7C.

Figure 7A:
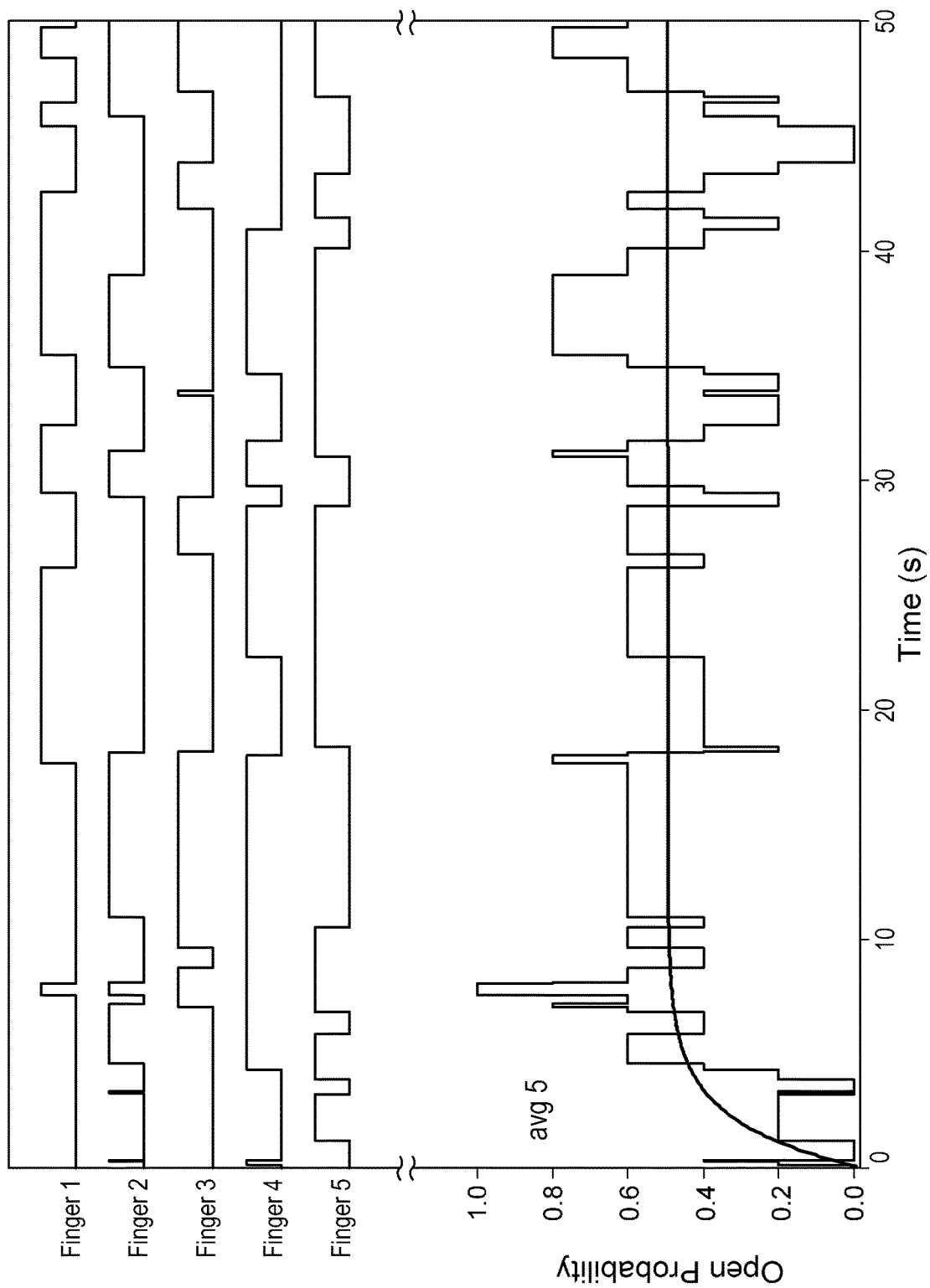
FIGS. 7A, 7B and 7C illustrate the analysis of the 2-state model for a set of illustrated finger movements with $\alpha=\beta=0.25/s$, where all fingers are in the closed state at t=0.
Figure 7B:
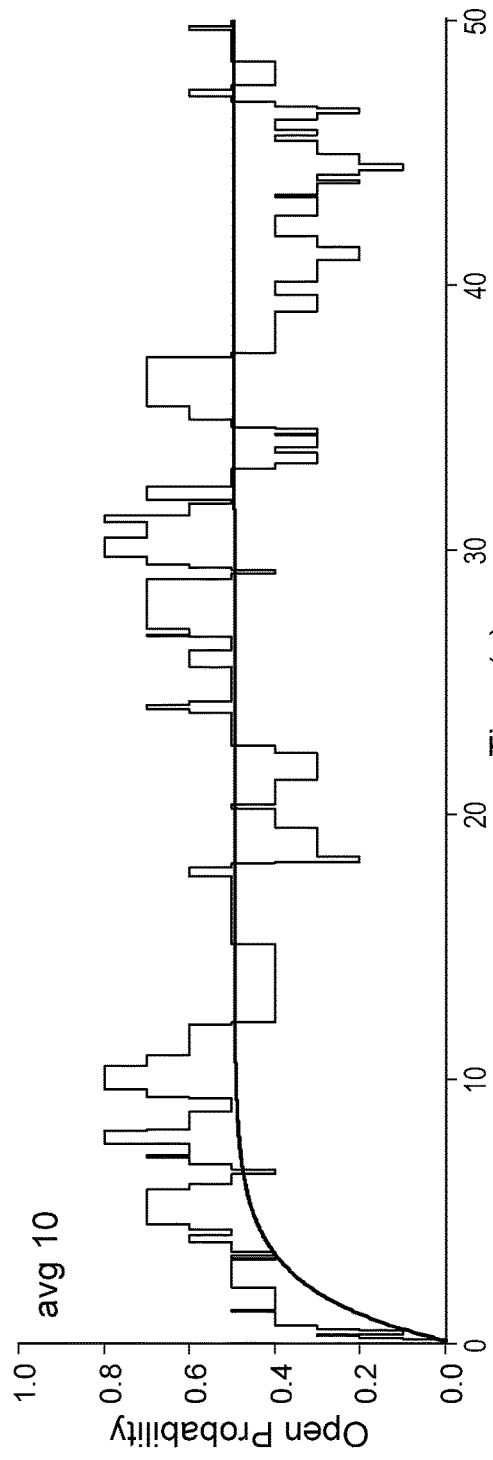
Figure 7C:
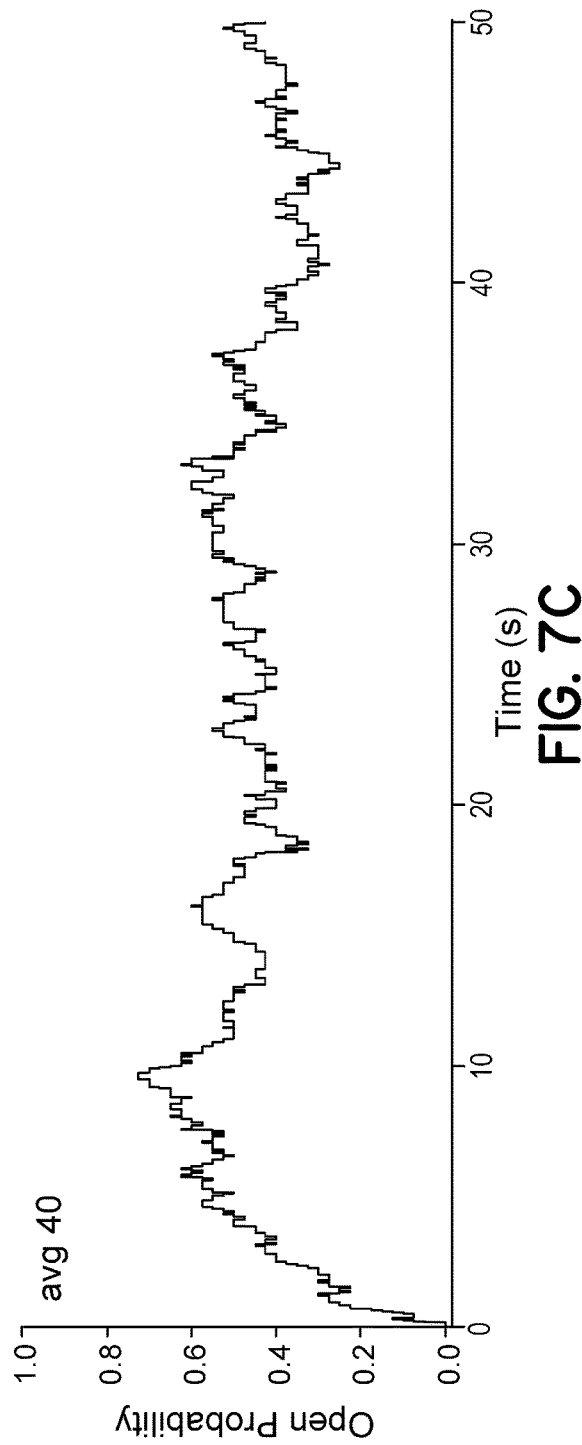

FIGS. 7A, 7B and 7C specifically illustrate analysis of 2-state model with $\alpha=\beta=0.25$/s and all fingers are in the closed state at t=0.

In FIG. 7A, one can see the average of the movements of the individual fingers (1-5), which are shown separately and plotted on the same time scale as their average. The smoothly curved line shows the predicted time course.

In FIG. 7B, one can see the average of 10 individual single finger sweeps which conforms more closely to the predicted time course.

In FIG. 7C, one can see the average of 10 individual single finger sweeps repeated 4 times for a total of 40 sweeps, which conforms even more closely to the predicted time course.

Increasing Model States and Complexity

Building upon the above concepts and approaches, this section will now describe how the computer program expands the 2-state model to include additional states.

For example, let us consider a 3-state model where the hand can exist in a closed fist, open palm, or a blocked position. The open palm state is a functional position of interest (e.g., approaching an undesired position where the hand is open to grasp an object). The closed state is the opposite of open, and the "blocked" position is distinct from the closed state. Both the blocked and closed states are not a functional position of interest. Analysis of movement records during the initial training period reveals the sequential occurrence of events such that the closed state always preceded the open state and vice versa, and the blocked state always preceded the open state and vice versa. Based on this sequential ordering of observed states, the program will construct the following model:

Model 2

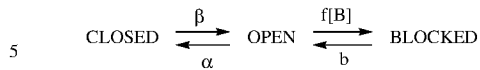

This model can describe the interaction of a hand with an undesired object. It assumes that once a hand is in the open state, the person can grasp the object. The blocked state can occur when the hand has grasped the undesired object. Model 2 is a sequential model because only the open hand can lead to the blocked state.

Note that Model 2 has two additional rate constants (f and b) and a term quantifying the number of undesired objects in the proximity space of the hand:

f=the forward blocking rate or the association rate constant (units 1/density/s).

b=the backward (release) rate or the dissociation rate constant (1/s).

[B] is the proximity density of the undesired object; if the undesired object is not in proximity, then the model will simply collapse to become Model 1 (i.e., with only two states).

The mathematical procedures for solving the 3-state model are similar to those used for the 2-state model. The equation describing the time rate of change of closed fingers is the same as it was in the 2-state model (there's no other place for the closed fingers to go) (see Eq. 13 below, compare to Eq. 3)

$$\frac{dN_c}{dt} = -\beta N_c + \alpha N_o \quad \tau_c = \frac{1}{\beta} \quad \text{Eq. 13}$$

In the three state model there are two routes that the open fingers can follow, to the closed state or to the blocked state. This is described mathematically as:

$$\frac{dN_o}{dt} = \beta N_c - \alpha N_o - f[B]N_o + bN_b \quad \tau_o = \frac{1}{\alpha + f[B]} \quad \text{Eq. 14}$$

The equation for the blocked position has just two terms:

$$\frac{dN_b}{dt} = f[B]N_o - bN_b \quad \tau_g = \frac{1}{b} \quad \text{Eq. 15}$$

Equations 13-15 are solved by equations of the form:

$$N_c(t) = N_{c1}\exp(-\lambda_1 t) + N_{c2}\exp(-\lambda_2 t) + N_{c3} \quad \text{Eq. 16}$$

$$\tau_b = \frac{1}{\alpha} + \frac{f[B]}{\alpha b}$$

If a model has m number of states, the solutions will contain m−1 exponential terms, which will be constructed by the computer program in a similar manner. The solutions for $N_o$ and $N_b$ have a similar form.

$$N_o(t) = N_{o1}\exp(-\lambda_1 t) + N_{o2}\exp(-\lambda_2 t) + N_{o3}, \quad \text{Eq. 17}$$

$$N_{o/b} = 1 + \frac{f[B]}{\alpha}$$

-continued $$N_b(t) = N_{b1}\exp(-\lambda_1 t) + N_{b2}\exp(-\lambda_2 t) + N_{b3} \quad \text{Eq. 18}$$

Equilibrium occurs when all of the time derivatives equal zero. Using $N_t = N_c + N_o + N_b$ and some algebra:

$$\frac{N_o}{N_t} = \frac{\beta/\alpha}{1 + \frac{\beta}{\alpha}\left(1 + \frac{f[B]}{b}\right)} \quad \text{Eq. 19}$$

By setting [B]=0, Eq. 19 reduces to Eq. 2, the 2-state result. As [B] increases, the number of fingers in the open state decreases. The form of Eq. 19 is a rectangular hyperbola. This may be easier to see if we write it as:

$$I = \frac{I_{max}}{1 + I_{max}\frac{f[B]}{b}} \quad \text{Eq. 20}$$

where, $I_{max} = \beta/(\alpha+\beta)$ (refer to Eq. 2). The form is also like the Michaelis-Menton equation from biochemical reactions, or the Hill equation with $n_H=1$, or the Langmiur isotherm. If $I_{max}=1$, then $$I = \frac{1}{1 + \frac{[B]}{K_i}} \quad \text{Eq. 21}$$

where $K_i = b/f$.

Figure 8:
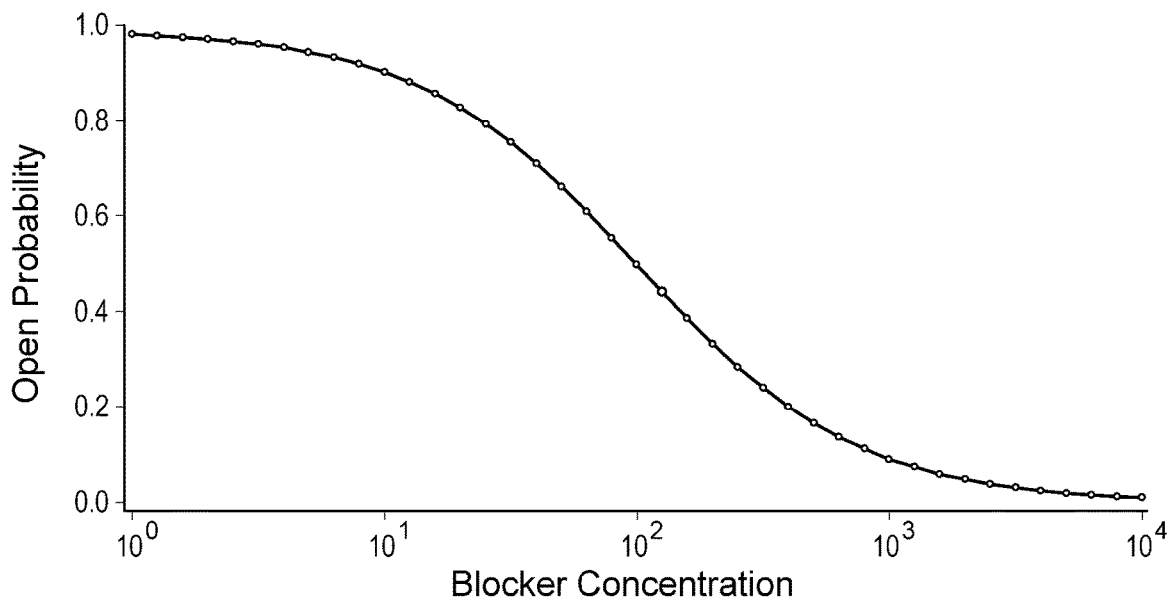
FIG. 8 illustrates, for a three-state model featuring closed, open, and blocked states, model predictions of the probability of the open state.

This is drawn in FIG. 8 where "Blocker Concentration" represents the proximity density of the object, for a steady-state in which $\beta=100$/s, $\alpha=1$/s, $f=0.01$/s, $b=1$/s.

Figure 9:
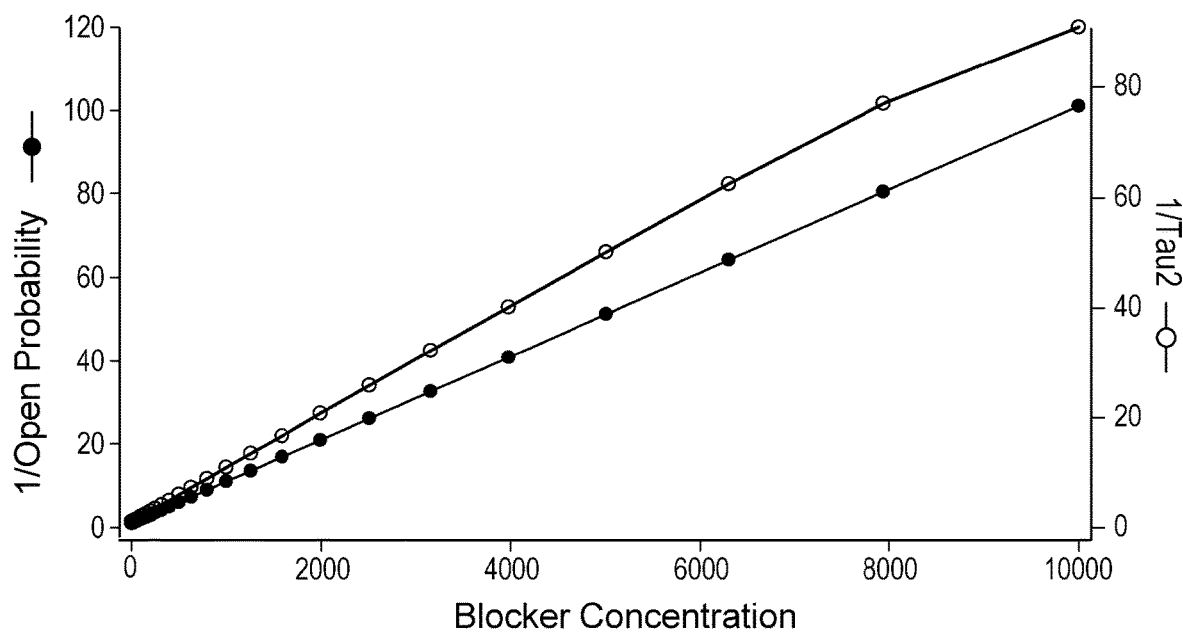
FIG. 9 illustrates model predictions of the reciprocal of the probability of the open state for the conditions used in FIG. 8.

By taking the reciprocal of Eq. 18, 20 or 21, we can see that $N_t/N_o$ is a linear function of the proximity density of the object. The slope of this line is $f/b=1/K_i$, which is illustrated in FIG. 9 for $\beta=100$/s, $\alpha=1$/s, $f=0.01$/s, $b=1$/s.

Equations 16-18 contain two rate constants, $\lambda_1$ and $\lambda_2$. They come from solving a quadratic equation.

$$\lambda_{1,2} = \frac{-(\beta + \alpha + f[B] + b) \pm \sqrt{(\beta + \alpha + f[B] + b)^2 - 4(\beta b + \alpha b + \beta f[B])}}{2} \quad \text{Eq. 22}$$

We can simplify this if the gating process (involving $\alpha$ and $\beta$) is much faster than the transition to the blocked state (involving f[B] and b). In this case, one time constant is fast and the other is slow. The slow time constant is due to transition to the blocked state.

$$\tau = \frac{1}{f[B] + b} \quad \text{Eq. 23}$$

The underlying assumption is that gating from one state to another is a simple Markov process. This means that the probability that a hand opens or closes is constant in time. The probability depends only on the present state of the hand, not on the state of the hand at earlier times.

Mathematical expressions derived from the 3 state model indicates that the mean lifetime of any state is equal to 1/(sum of rates exiting from the state). This, the average closed, open and blocked state times are:

$$\tau_c = \frac{1}{\beta} \quad \text{from Eq. 13}$$

$$\tau_o = \frac{1}{\alpha + f[B]} \quad \text{from Eq. 14}$$

$$\tau_g = \frac{1}{b} \quad \text{from Eq. 15}$$

There are two additional measurements that can be made on microscopic single finger analysis: the burst duration ($\tau_b$) and the number of openings per burst ($N_{o/b}$). The burst duration can be a sub-state (e.g., the finger does not fully open but flickers back and forth), which involves the finger opening but doing so via a distinct positional change or activity than characterized by the typical finger opening that has been described in the 2-state model or the finger grasping the object as in the 3-state model.

$$\tau_b = \frac{1}{\alpha} + \frac{f[B]}{\alpha b} \quad \text{from Eq. 16}$$

$$N_{o/b} = 1 + \frac{f[B]}{\alpha} \quad \text{from Eq. 17}$$

Figure 10:
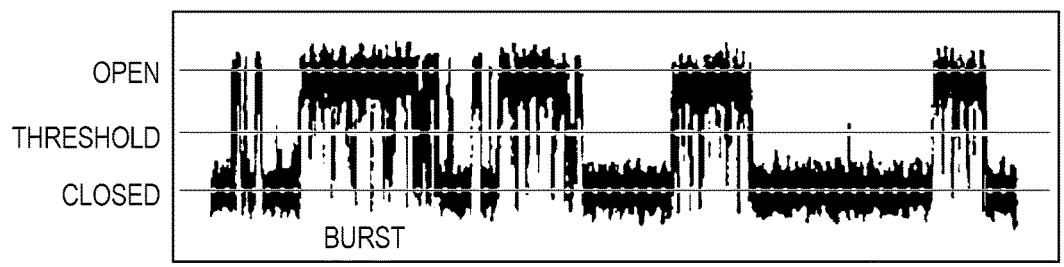
FIG. 10 is an illustration of burst activity of changes between closed and open states, predicting for example the tapping of a finger on an object, and illustrating the establishment of a threshold defining the open and closed states.

Equations 13-17 actually over specify the problem; there are 5 equations and only 4 unknowns. This is because the equations are not completely independent. For example, the burst duration can be written in terms of the open duration, the gap duration and the number of openings per burst. This is illustrated in FIG. 10. An example of burst activity would be the finger tapping on the object rapidly but without staying on the object.

$$\tau_b = N_{o/b}\tau_o + (N_{o/b}-1)\tau_g \quad \text{from Eq. 16.}$$

The threshold shown in FIG. 10 defines the opening and closing of states. This is determined by an iterative calculation that considers all possible values of the threshold and then selects the one that would result in the maximum number of openings and closings (i.e., crossings of the threshold value). Multiple distinct magnitude of openings (representing other distinct states) would be determined by additional thresholds, which would be set at an optimal value via the iterative routine. The gap duration represents the microstate of the finger making contact with the object for a short duration when it is tapping the object.

The presence of an object occupying the hand in the blocked position would not change the open time per burst. The person may keep track of how long the open finger has been open and then can close it instead of going into the blocked position again. Note that this would not follow our assumption that finger gating is a Markov process (which assumes that the past history of a finger does not determine its future). This will be accounted for by Graph theory and artificial intelligence (as explained below).

Determining Rate Constants in the Model from the Data of the Finger Movements

Note that the gap duration does not depend on [B], i.e., the proximity density of the object. The reciprocal of the gap duration is the unblocking rate constant, so this only accounts for the time it takes for the finger to come off the object once the finger has already made contact with the object. So, by definition, the object must already be close enough for the finger to have made contact with it.

Figure 11A:
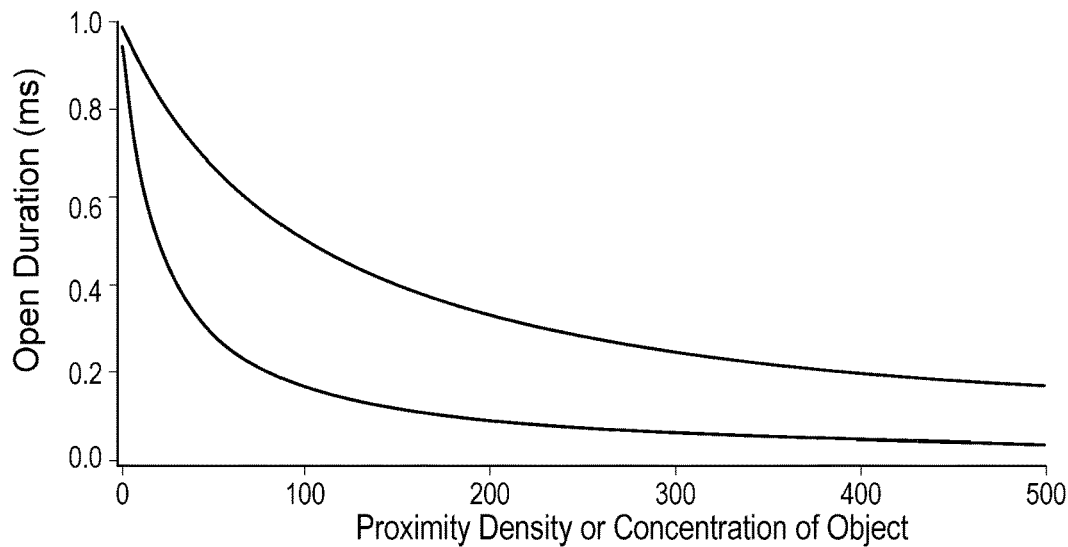
FIG. 11A is a histogram of the closed state durations for the three-state model and FIG. 11B is a histogram of the reciprocal of the open state durations for the same model.
Figure 11B:
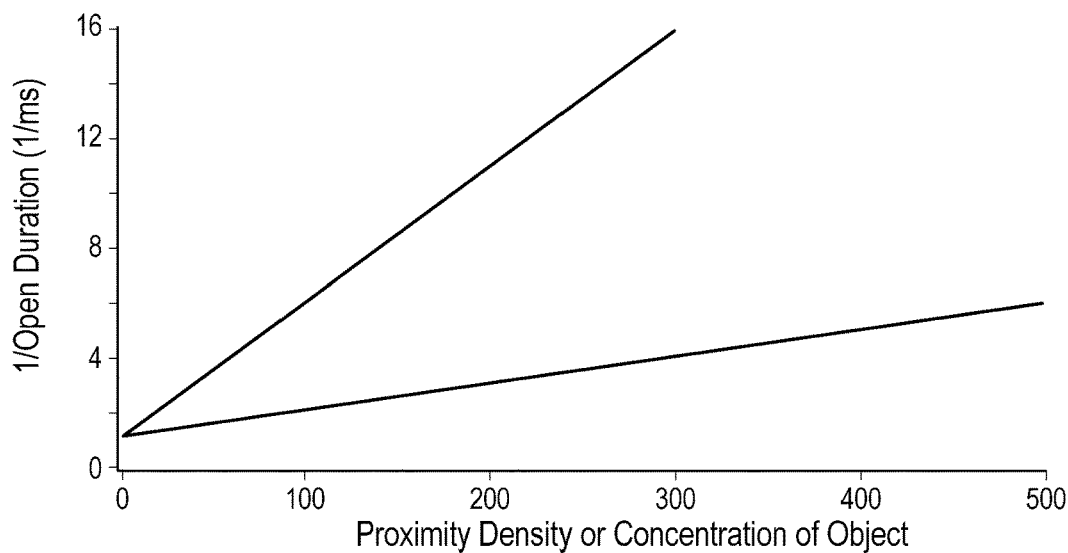

However, the open duration does depend on [B]: openings become briefer as the proximity density of the object is increased, as seen in FIG. 11A. Plotting these data as $1/t_o$ vs. [B] reveals a linear relationship, as seen in FIG. 11B. The slope of the line is the blocking rate constant and Y-intercept is the finger's closing rate, $\alpha$.

Linear relationships also exist between the blocker concentration and the burst duration (Eq. 16) and the number of openings per burst (Eq. 17). Now, consider the distribution of "dwell times" that result from the 3-state model, that is, the open, closed and burst durations.

Figure 12A:
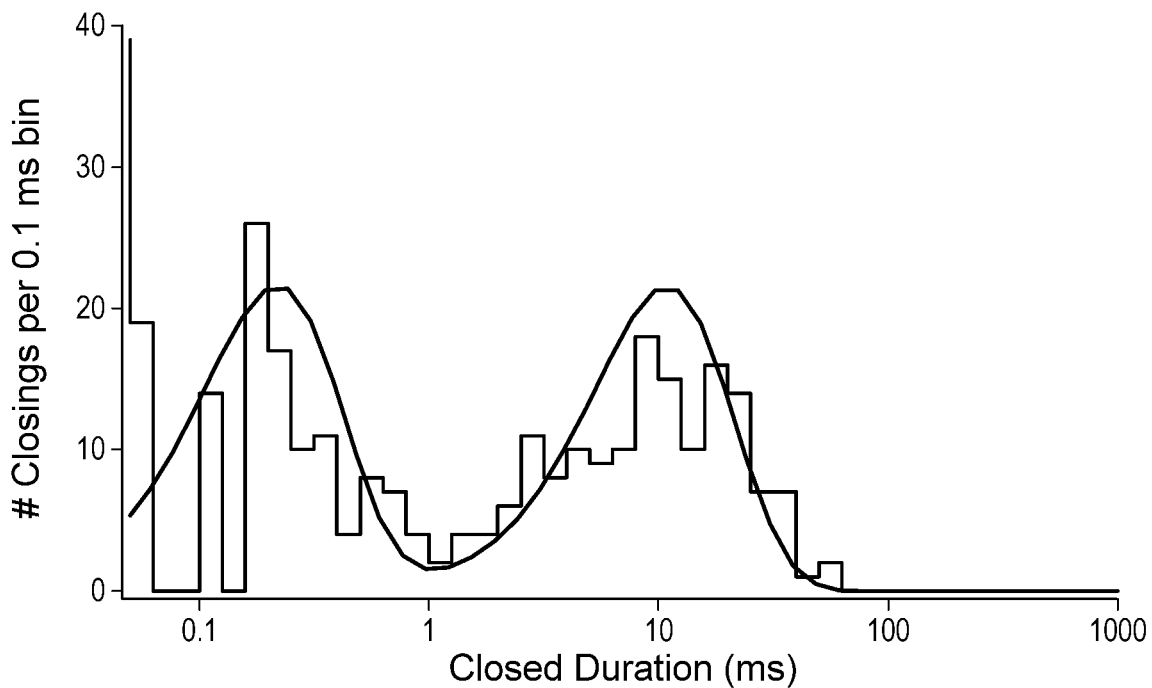
FIG. 12A is a histogram of closed time for a three-state model.
Figure 12B:
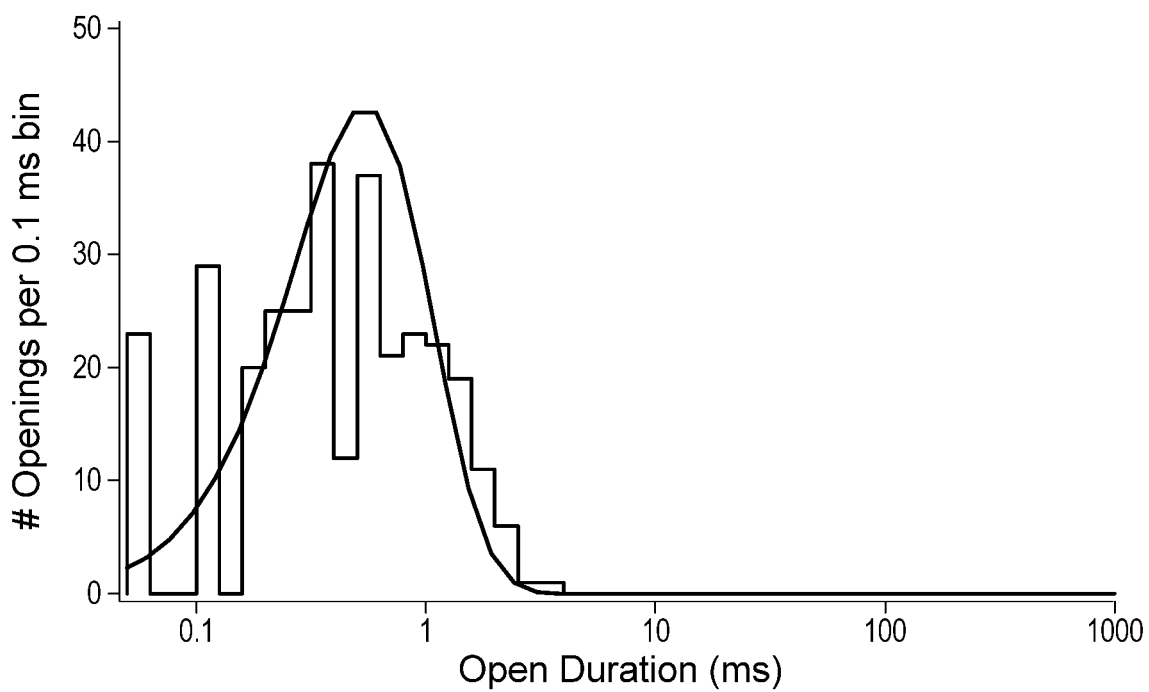
FIG. 12B is an open time histogram for the same model and same parameters.

A general rule employed in computing these data is that each closed state in the model contributes a component to the closed time histogram. The same is true for the number of open states. FIG. 12A is a closed time histogram for the 3-state model with $\beta=0.01/ms$; $\alpha=1/ms$; $f=0.01/ms$; $b=5/ms$; $[B]=100$; average of 313 events. The 3-state blocking model has 2 closed states and thus 2 components are seen in the closed time histogram. FIG. 12B is an open time histogram for the 3-state model with the same parameters. Note that there is only 1 open state in the model, so there is just one open time component. Similarly, there is only 1 way to produce a burst: $C \rightarrow (O \rightarrow B)_n \rightarrow C$ Thus, the burst duration histogram has just 1 component.

Determining Rate Constants from the Macroscopic Data of the Hand Movements

The equation describing the time rate of change of closed fingers is the same as in the 2-state model because there is no other place for the closed finger to go (i.e., refer to Eq. 3).

$$\frac{dN_c}{dt} = -\beta N_c + \alpha N_o \qquad \text{Eq. 24}$$

Now there are two routes that the open hand can follow, closed or blocked. This is described mathematically as:

$$\frac{dN_o}{dt} = \beta N_c - \alpha N_o - f[B]N_o \qquad \text{Eq. 25}$$

$$\tau_o = \frac{1}{\alpha + f[B]}$$

The equation for the blocked hand has just two terms:

$$\frac{dN_b}{dt} = f[B]N_o - bN_b \qquad \text{Eq. 26}$$

$$\tau_g = \frac{1}{b}$$

Equations 24-26 are solved by equations of the form:

$$N_c(t) = N_{c1}\exp(-\lambda_1 t) + N_{c2}\exp(-\lambda_2 t) + N_{c3} \qquad \text{Eq. 27}$$

$$\tau_b = \frac{1}{\alpha} + \frac{f[\beta]}{\alpha b}$$

Similar expressions hold for $N_o$ and $N_b$.

As stated above, for a model with m states, the solutions will contain m−1 exponential terms. The two exponential rate constants are $$\lambda_{\pm} = \frac{-(\beta + \alpha + f[B] + b) \pm \sqrt{(\beta + \alpha + f[B] + b)^2 - 4(\beta b + \alpha b + \beta f[B])}}{2} \qquad \text{Eq. 28}$$

Equilibrium occurs when all of the time derivatives equal zero. Using $N_r = N_c + N_o + N_b$ and some algebra, we get $$\frac{N_o}{N_t} = \frac{\beta/\alpha}{1 + \frac{\beta}{\alpha}\left(1 + \frac{f[B]}{b}\right)} \qquad \text{Eq. 29}$$

Figure 13:
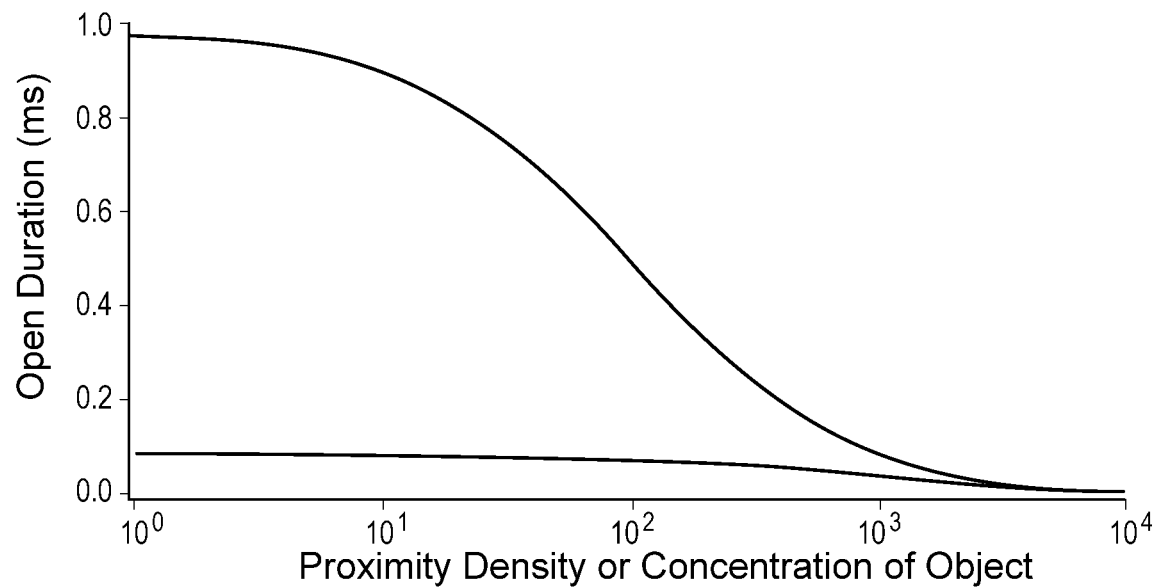
FIG. 13 is a probability prediction for open state probability for a three-state model.

By setting [B]=0, Eq. 28 reduces to Eq. 2, the 2-state result. As [B] increases, the number of fingers in the open state decreases. The form of Eq. 27 is a rectangular hyperbola. This may be easier to see if we write it as:

$$I = \frac{I_{max}}{1 + I_{max}\frac{f[B]}{b}} \qquad \text{Eq. 30}$$

where, $I_{max} = \beta \div (\alpha+\beta)$ (refer to Eq. 2). The form is also like the Michaelis-Menton equation, or the Hill equation with $n_H=1$, or the Langmiur isotherm, seen in FIG. 13. FIG. 13 shows blocking model predictions for steady-state open probability with $\beta=100/ms$ (0.1/ms for curve 2); $f=0.01/$concentration/ms; $\alpha=1/ms$; and $b=1/ms$.

Figure 14:
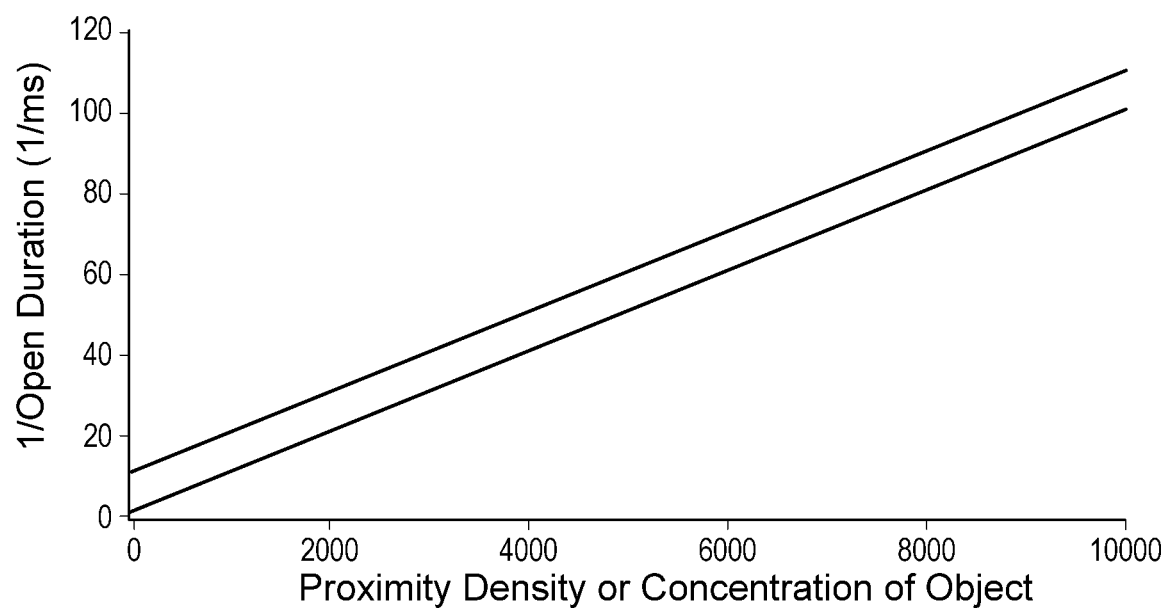
FIG. 14 is a reciprocal plot of the open state probability predictions of FIG. 13.

By taking the reciprocal of Eq. 29 or 30, you can see that $N_t/N_o$ is a linear function of the blocker concentration. The slope of this line is $f/b=1/K_i$ seen in FIG. 14, which is a reciprocal plot for the three state model predictions shown in FIG. 13.

While the rate constants of equation 28 can be analytically solved for a 3-state model, they will be impossible to analytically solve when additional states are incorporated into the model. Thus, numerical integration (e.g., Euler's method, Runge Kutta) is used to solve the rate constants.

The importance of using Markov models is to collapse data from multiple sources to form the principle states. The example discussed thus far has only been that of a hand movement in a single dimension. Incorporating additional dimensions of movement and from different sources of measurement (e.g., video camera, accelerometer) can be incorporated to construct a single model of an individual. This is preferred over forming different models, each from a different measure and then comparing and collapsing the states. The reason is that each state is coupled such that changes in one can affect others. For example, closing a hand about a bedrail (movement to blocked state) can be linked to sitting up in bed. Thus, constructing the model at each step of defining the states will lead to more accurate and precise model generation. For example, an accelerometer may be more accurate than a camera measurement of movement toward or away from the sensor, whereas the camera measurement may be more accurate in another direction. As such, during model generation, data from one source and/or dimension may be weighed more than another when some parameters of a state defined by each method are not consistent. By accounting for this at each step of the process during model generation will lead to more accurate and precise model generation for the subsequent states.

Building the Comprehensive Personalized Predictive Model

While Markov models will be constructed to identify the key rate-limiting states and their rate constants, Graph theory will be employed to incorporate the memory of what has occurred in the past and earlier states and to establish multi-dimensional relationships between states. This was first used by Leonhard Euler to solve the famous Königsberg Bridge Problem. The basic premise is that the relationship between states plotted as sets of ordered pairs, G=(V, E), comprising a set V of vertices or nodes or points together with a set E of edges or arcs or lines, can be used to define whether any number of states are either directly connected by a transition gate. In general, V is a set together with a relation of events that associates two vertices with each edge. In another generalized notion, E is a multiset of unordered pairs of (not necessarily distinct) vertices, e.g., multigraph or pseudograph, to incorporate all dimensions and body regions. See Leonhard Euler, Commentationes Arithmetica Collectae, St. Petersburg (1766) 66-70 and http://www.zib.de/groetschel/teaching/WS1314/Bondy-MurtyGTWA.pdf each of which is incorporated herein in its entirety.

Figure 15:
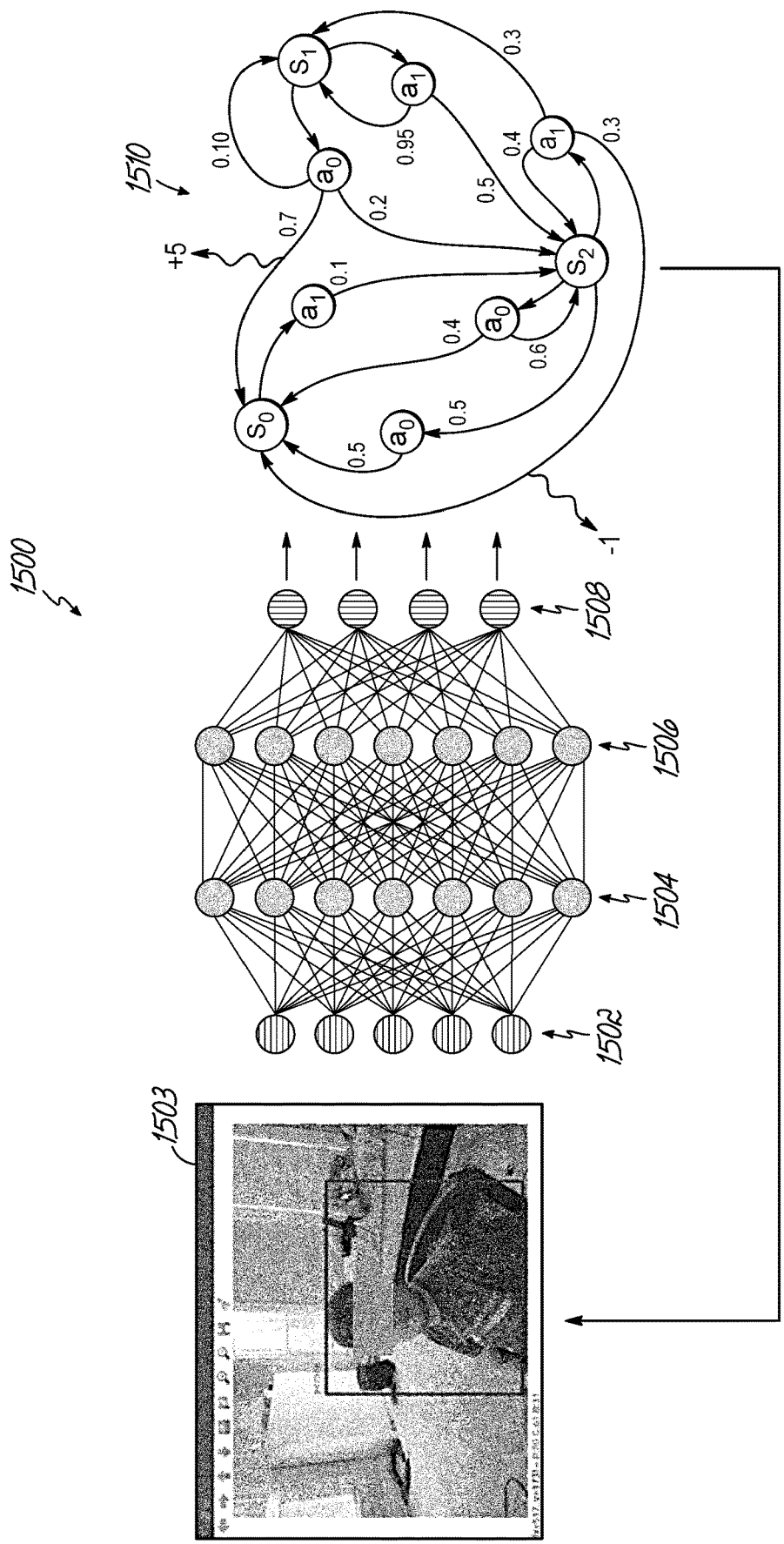
FIG. 15 is an illustration of the use of Markov kinetic modeling with predefined actions combined with Graph theory, used to trail probabilities of state transitions in an individual, and the use of unsupervised classification to generate new states/actions to continue to refine the model.

Referring now to FIG. 15, Markov kinetic modeling with predefined actions may be combined with Graph theory to train probabilities of state transitions in an individual, which may be used and then use unsupervised classification to generate new states/actions to continue to refine the model.

As noted above with reference to FIG. 1, after an initial training component using current and prior training sets, the self-optimizing "smart" artificial intelligence algorithms according to principles of the present invention will reiteratively compare between predicted and actual outcomes of the model to allow for a "learning" component by (1) adjusting weights of independent states as predictors for events in an individual, (2) augmenting and improving data analysis, and (3) collecting more data. In case of the need to augment inputs and expand analysis, the integrator can self-replicate and extend its components to include new input sources and analyses. During training, model parameters will be learned by cross-validation, i.e., a leave-one-out strategy for all the states in the model as the training set to evaluate the predictive capacity on the held-out state. This will be repeated per model to obtain individualized prospective data.

The computer program according to principles of the present invention will identify optimal predictors to achieve the highest possible predictive accuracy while utilizing cross-validation to minimize overfitting. After pre-processing (e.g., standardization, normalization, reclassification), an iterative process of feature engineering, feature selection, model generation and model/feature assessment will identify useful features for prediction. Predictors with missing values will be excluded. Once key features are identified, methods such as k-means and hierarchical agglomerative clustering will be used to find similar groups of data corresponding to identifiable states (or other novel states that merit further study). In cases where well-defined classes of events or outcomes are available (e.g., undesired position, movement or activity), feed-forward neural networks will be trained to assign individual states to these classes.

An advantage of using such neural networks is that, by using convolutional layers, time-series data can be combined directly with static features within the same classifier, resulting in sophisticated multi-modal classification. This can be used for prediction by taking future states as the classes. In addition, time-series data can be used directly for predicting their future course using recurrent neural networks. Machine learning will also be used to visualize high-dimensional data in 2-D or 3-D spaces.

Referring now to FIG. 15, reference may be made to a simplified schematic example 1500 of a personalized predictive kinetic state model based on continuous AI monitoring and analysis of the most frequently occurring positions and amount of time spent in the positions, sequential ordering of positional changes, and rates of transition from one position to another, calculation of probabilities, conditional probabilities and confidence intervals of entering an undesired position that can lead to an event (e.g., patient fall in a hospital setting). The illustrated convolutional neural network includes an input layer 1502 comprising a plurality of inputs such as a video input 1503 showing an individual in a monitored setting. The network further includes multiple hidden layers 1504, 1506, etc. implementing Markov kinetic modeling combined with Graph theory and artificial intelligence to generate personalized models. One or more states $S_0$, $S_1$, $S_2$ seen in the state model 1510. The transitions between states can be comprised of additional kinetic models and transitions at different time scales and/or volume spaces to identify unique signatures of the individual. At an output layer 1508, different types and levels of actions $a_0$, $a_1$ can be automatically deployed to prevent the predicted fall when the individual is predicted to enter high, higher and highest risk positions (not shown). Whereas all current methods for predicting the event operate around the time of the event occurrence, the current invention will use the personalized model to predict the event before it happens.

Figure 16:
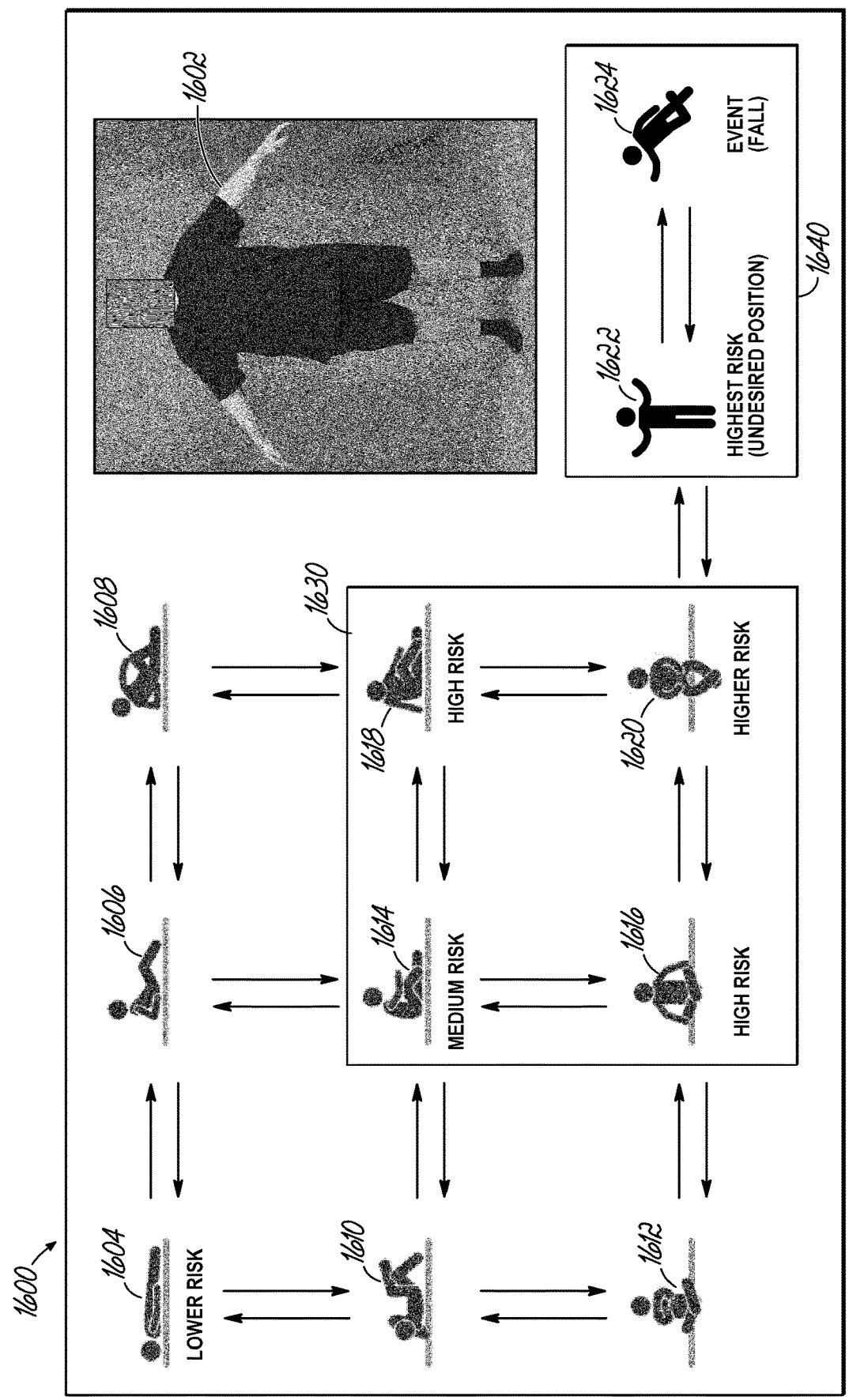
FIG. 16 is a simplified schematic example of a personalized kinetic state model based on continuous monitoring and analysis of the most frequently occurring positions and amount of time spent in those positions, and sequential ordering of position changes, and rates of transition therebetween.

FIG. 16 illustrates a particular exemplary set of model states 1600 for an individual 1602 under observation by a system according to principles of the present invention. The individual's posture is modeled by several states or bodily attitudes 1604-1624. These are then further characterized by transitions, e.g., the transition from a prone position 1604 to either a propped prone position 1606 or a cross-legged prone position 1610, which precede transitions to other, positions such as a side propped prone position 1608 or a seated position 1612.

Position states may be classified as lower or greater risk, representing the risk of a fall in a hospital, hospital or nursing home setting. Risk-bearing states 1630 may be identified for actions/warnings based upon their likelihood to lead to high risk positions. E.g., a seated position 1614 on the bed with knee movement may lead to departure from the bed, and this risk his higher in the case of a position 1620 indicating for exit from the bed, a bedside seated position 1616 where the legs are preparing for leaving the bed, and the risk is further elevated in position 1620 where the legs are off of the bed and one more state movement can lead to a standing position 1622. The standing position 1622 and any subsequent states such as falling 1624 can be identified as highest risk states 1640, and lead to further or more urgent actions or warnings.

Figure 17A:
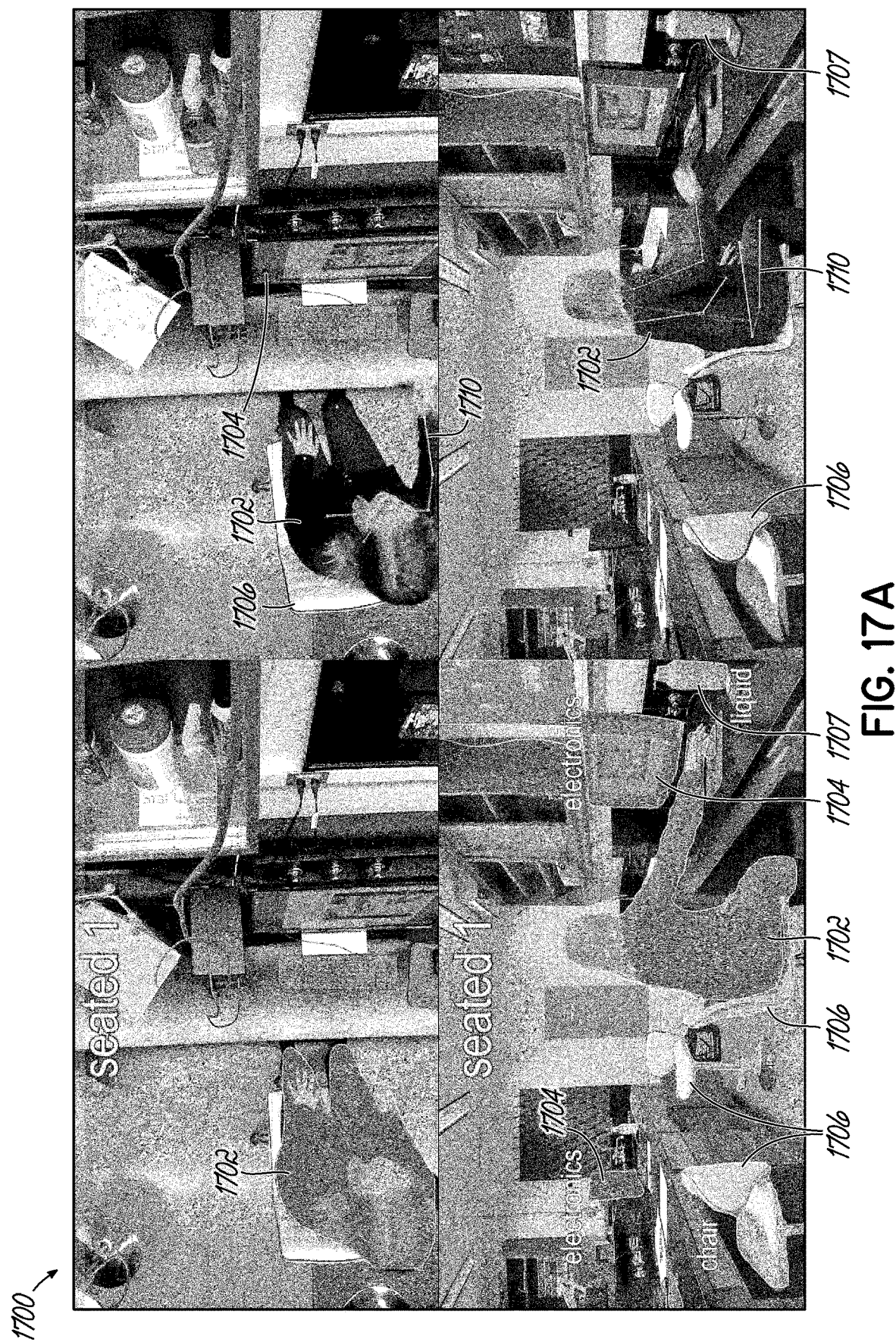
FIGS. 17A, 17B, 17C, 17D and 17E are illustrations of movements of an individual in an observed environment which are captured by a system according to the present invention and used to build and evolve a state transition model.
Figure 17B:
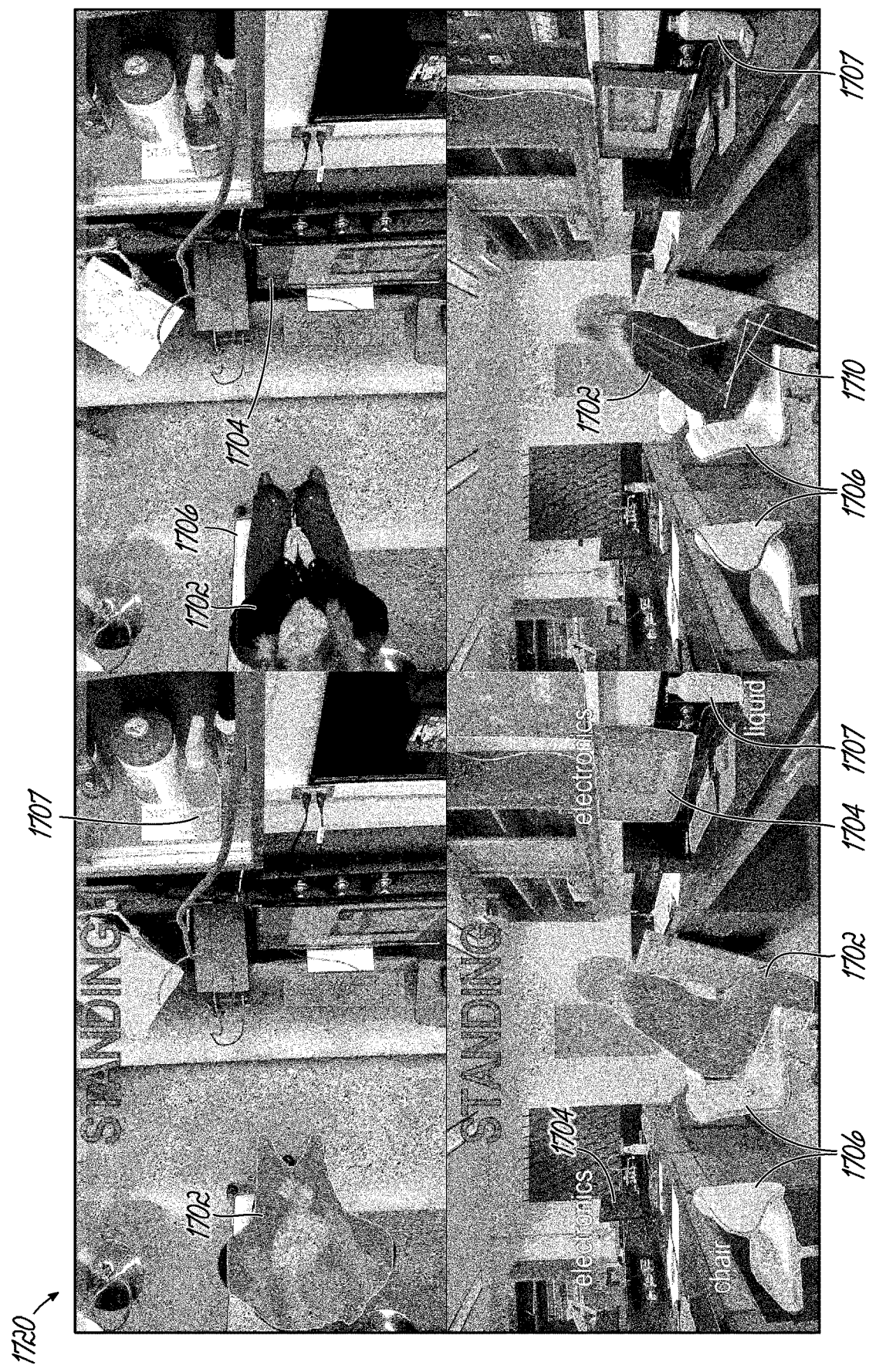
Figure 17C:
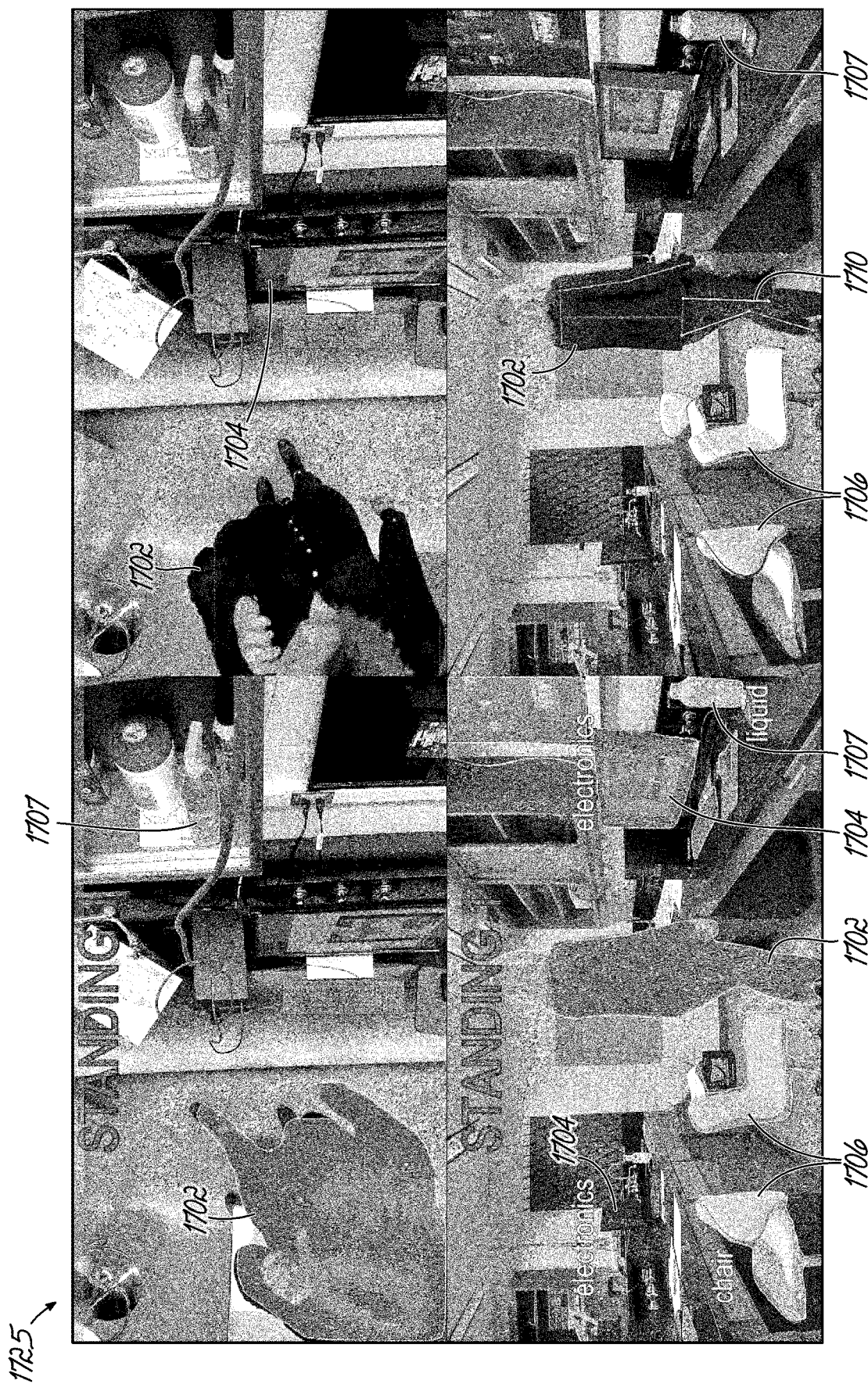
Figure 17D:
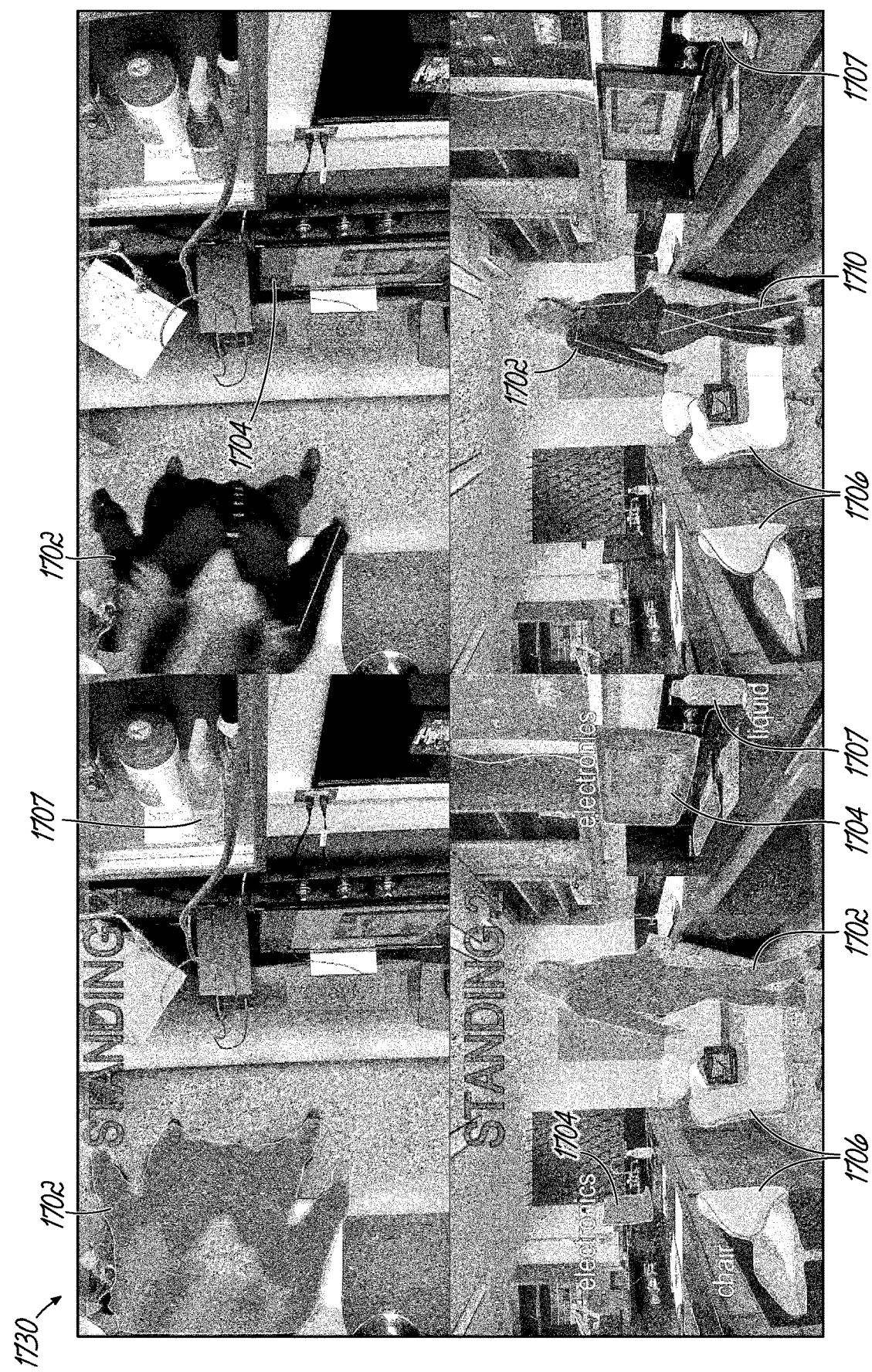
Figure 17E:
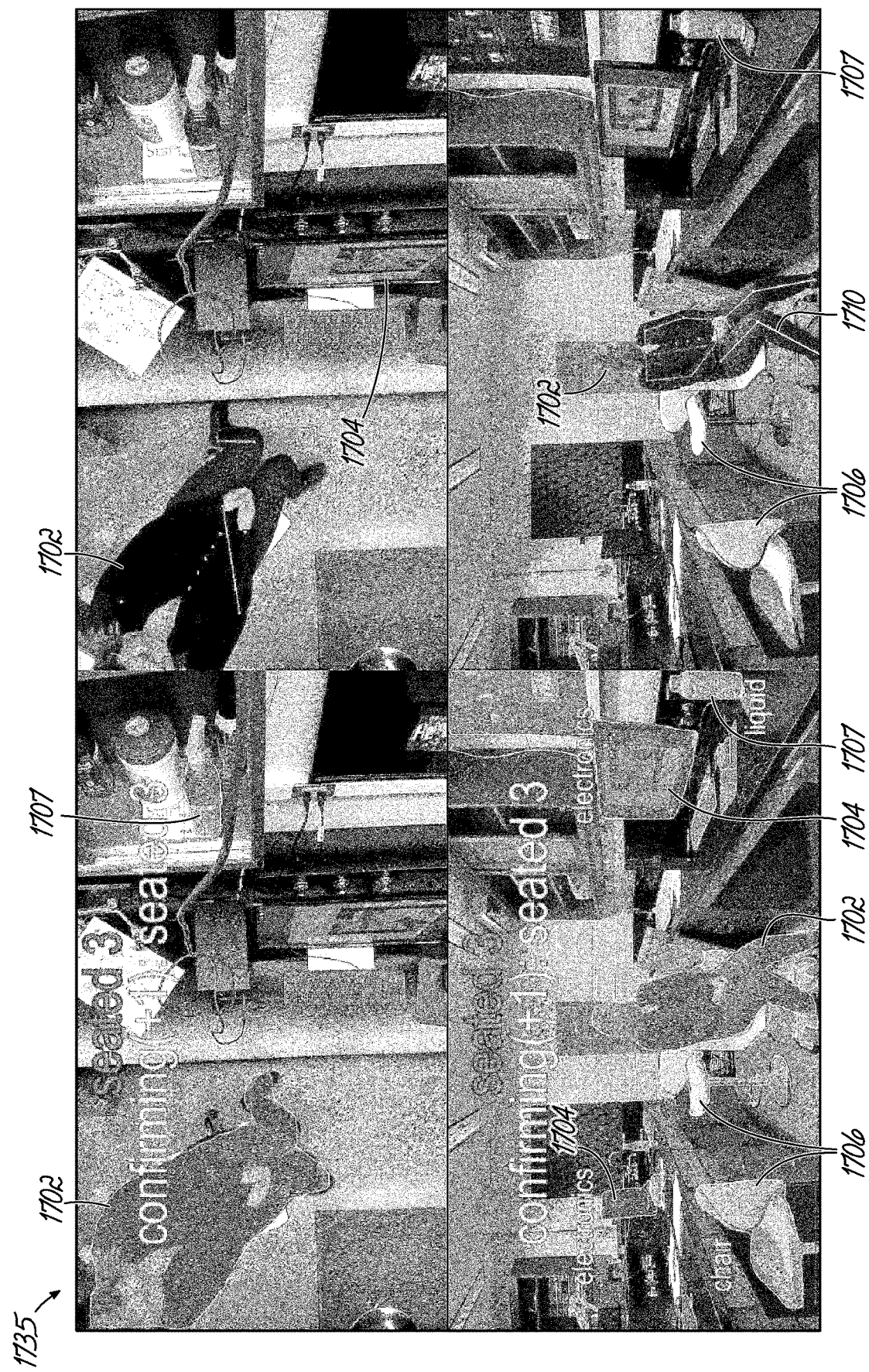
Figure 18:
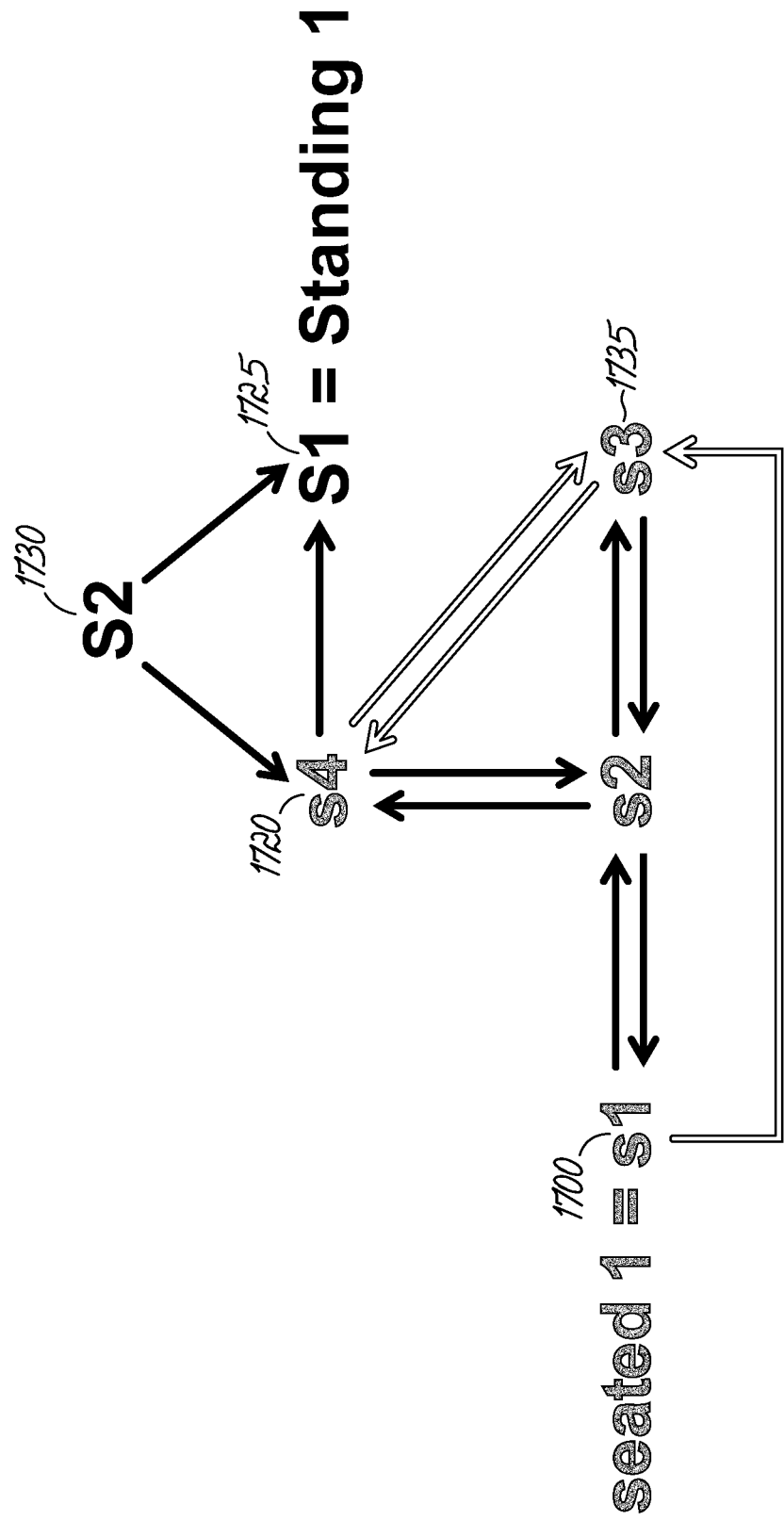
FIG. 18 illustrates a state transition model developed in response to the movements illustrated in FIGS. 17A-17E.

The present invention may be enhanced by the capture of interaction of a person with an environment, as seen in FIGS. 17A through 17E, which show movements between states illustrated in FIG. 18.

In FIG. 17A, an individual 1702 is captured in a seated position 1700 on one of several chairs 1706, adjacent to electronics 1704, a liquid container 1707 and other environmental elements. The individual's limb positions can be captured in a kinesthetic model, as seen at 1710, and these positions used in a multi-variable model to define the individual in position 1700 as in a seated state, which is near to a working station as indicated by the nearby recognized electronics, chairs and beverage. This position is seen in FIG. 18 identified as an s position 1700, representing a stable position for work by an individual.

If the individual 1702 moves the chair away from the electronics and workstation, this will be a distinctly identifiable condition, and can be captured as a second seated state in the Markov model. This position is designated as seated position 2 or s2 in FIG. 18.

In FIG. 17B, the individual 1702 has not only moved the chair away from the electronics, the individual has changed the attitude of the individual's torso, knees and arms 1710, indicating movement toward a still further position. This state 1720 is thus captured for distinction from the s1 state 1700 and the s2 state, for development of the behavioral model. Eventually this state will be identified as a transitional seated position s4 distinct from the previously delineated s1 seated position state 1700 and s2 seated position.

In FIG. 17C, the individual 1702 is now standing as indicated by torso, arm and leg positions 1710, but remains near to a chair, thus defining a further evolution of kinetic attitude, and leading to the establishment of a first standing position state or S1 1725. In light of the evolution of the individual to this position, the Markov model now includes several seated states: seated state s1 1700, seated state s2 which can be reached from s1, and seated state s4 1720 which can be reached from seated state s2. Further, the model evolves to include a standing position S1 1725 which can be reached from seated position s4 1720.

In FIG. 17D, the individual 1702 is fully erect and has begun ambulating in the room away from the chair, and is thus is identified as in a further distinct kinetic state 1730. This state is distinguishable from the previous positions 1700, 1720 and 1725 by captured body/limb positions 1710 and adjacency of furniture and other recognizable objects. As a result, the Markov model may be refined to define state 1730 as a second standing state S2.

In FIG. 17E, the individual 1702 has returned to the chair but the chair is pushed back from the workstation and rotated away from it. This state is distinct from previously seen seated states, and is thus recognized as a further distinct state 1735 and designated as seated state s3, which is added to the existing model, along with identification of the states which might precede or follow it.

Via the foregoing process, an advanced Markov model is learned and developed from observations of an individual over time to closely track both the movements of an individual and the associated states of motion which may follow a particular kinetic state. Further, probability weights may be developed describing the likelihood of each state leading to its neighboring states, so that accurate predictions may be made of forthcoming kinetic state changes before they occur, based upon an individual's historic kinetic activity.

The present invention has been described with reference to a particular embodiment, but the principles of the invention are applicable to numerous other applications and embodiments. Among other applications, the invention is also applicable in noncustodial environments, such as rehabilitation or athletic training facilities, where the principles of the invention may be applied to facilitating the rehabilitation, development and training of athletes and others for optimal exercise tolerance and athletic performance. Indeed, by tracking kinesthetic data against the results of a competitive athletic engagement (e.g., a tennis match), the invention may provide feedback and coaching to improve athletic performance such as by detecting trends in performance to reform. The same principle can be applied, for example, to baseball where hitters and pitchers may benefit from detailed evaluation of their athletic motions, football, basketball, soccer, and the like. By tracking the results of athletic competition or exercises, coaching and training regimens at a deep level not now available, the invention facilitates the development of new AI-based methods for unraveling unique mechanistic and performance insights that otherwise are not available from conventional approaches. Insights in athletic methods, training regimens and model ideal methods for a particular individual or population may be developed which are presently unknown.

While the present invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit or scope of applicant's general inventive concept.

What is claimed is:

1. A system for predicting kinesthetic outcomes from observed position, posture, behavior or activity of an individual, comprising a plurality of kinesthetic activity sensors each collecting one or more of audio, video, or physiological signals capturing the activity of the individual or an ambient environment of the individual;

a computer system connected to the kinesthetic activity sensors and implementing a learning routine responsive to multi-dimensional data from the kinesthetic activity sensors reflecting behavior, habits, activities and/or positional changes of the individual and the order in which they occur in the individual, the learning routine constructing one or more personalized kinetic state models of positional states for the individual and transitions between the positional states; wherein the learning routine further develops one or more customized multi-dimensional prediction models for the individual, and uses the multi-dimensional prediction models to predict behaviors, activities and/or positional changes likely to occur in the future; and a notification system initiating a notification, alert or warning upon prediction of a behavior, activity or positional change associated with an unsafe or undesired outcome, and transmitting the notification, alert or warning to a recipient associated with the individual, wherein the learning routine is responsive to data from electronic health or medical records and physiological signals to assess predictive accuracy of the personalized kinetic state model and modifies the kinetic state model based thereon.

2. The system of claim 1 wherein the recipient associated with the individual is one or more of:

a custodian or caretaker for the individual;

a coach or trainer for the individual;

a storage system for storing notifications, alerts or warnings.

3. The system of claim 1 adapted to prediction and prevention of falls in a hospital, clinical, ambulatory or home environment, wherein the recipient is a caretaker for the individual, and the notification, alert or warning relates to the likelihood of a fall by the individual.

4. The system of claim 3 wherein the data collection from the kinesthetic activity sensors is secured in a manner compliant with applicable rules and regulations of patient confidentiality.

5. The system of claim 1, wherein the physiological signals include but are not limited to changes in electrocardiography, respiration, temperature, blood pressure, saturation of blood oxygen, intracardiac pressures, electroencephalogram and positional signals.

6. The system of claim 1, wherein ambient environmental sources include but are not limited to haptic, accelerometric, gyroscopic, temperature, visual, auditory or positional changes of objects in the immediate vicinity of the individual.

7. The system of claim 1, wherein the kinesthetic activity sensors detect audio signals of all sound spectrums including but not limited to the frequencies of human hearing.

8. The system of claim 1, wherein the kinesthetic activity sensors capture video or images of visible, infrared, thermal and/or ultraviolet light.

9. The system of claim 8, wherein the video or images are acquired from a plurality of locations having visibility of the individual, and the learning routine identifies the position of key positional points for the individual in a three-dimensional Cartesian plane using a combination of video or images acquired from said plurality of locations.

10. The system of claim 1, wherein the kinesthetic activity sensors capture haptic, tactile, pressure, accelerometric, gyroscopic and/or temperature data from the vicinity of the individual.

11. The system of claim 1, wherein the behavior, activity or positional change associated with an unsafe or undesired outcome comprises one or more of an undesirable or unsafe change in position, posture, behavior or activity.

12. The system of claim 11 wherein the undesirable or unsafe behavior, activity or positional change is an unsteady gait of the individual.

13. The system of claim 11 wherein the undesirable or unsafe behavior, activity or position change is proximity of the individual to a harmful object.

14. The system of claim 1 wherein the learning routine comprises one or more of a supervised routine comprising linear and logistic regression, support vector machine, naive Bayes, neural network, gradient boosting, classification trees and random forest, and an unsupervised routine comprising K-means, hierarchical clustering or mixture models, dimensionality reduction, anomaly detections, reinforcement learning, or another feedback-based method.

15. The system of claim 1, wherein the learning routine comprises a deep structured learning, neural network.

16. The system of claim 1, wherein the learning routine is further responsive to data relating to the individual from electronic health or medical records.

17. The system of claim 1 wherein one or more of the kinesthetic activity sensors comprises a wearable device.

18. The system of claim 1 wherein the learning routine collects multi-dimensional data for more than one individual.

19. The system of claim 18 wherein the learning routine discerns the presence of different individuals using data from electronic health records and/or data from wearable devices.

20. The system of claim 1, wherein the learning routine identifies the individual and develops a personalized kinetic state model for the individual characterizing the behavior, preferred positions, preferred movement and rate of change in positions or movement of said individual.

21. The system of claim 1, wherein the learning algorithm predicts unsafe or undesired outcomes including sleeping, supine, sitting, getting up from a bed or chair, standing, ambulating, walking, unsteady gait, exercising, eating, in-between transition states, as well as other undesired or unsafe postures, positions or activities.

22. The system of claim 1, wherein the learning algorithm identifies events of predictive value of later behaviors, activities and/or positional changes.

23. The system of claim 22 wherein events of predictive value include: delivery of food; administration of sedatives; time since last bathroom visit; change in heart rate, respiration, pulse oximetry and/or electroencephalogram.

24. The system of claim 1 wherein the learning algorithm develops a prediction model from recurring behavior and personal habits of the individual based on one or more of: time of day and degree of recurrence and length of time spent in distinct postures, positions, behaviors or activities.

25. The system of claim 1 wherein the learning algorithm utilizes pooled data of similar individuals to develop an initial kinesthetic state model and starting conditions therefor, for subsequent personalization to the individual.

26. The system of claim 25 wherein personalization comprises one or more of adding states, subtracting states, ordering states, and developing rate constants for transition into and out of states.

27. The system of claim 1 wherein the learning routine constructs a personalized kinetic state model by adjustment of the number and description of and adjustment of rate constants and coefficients characterizing state transitions, based upon the match of predicted and actual changes in the individual's posture, position, behavior or activity.

28. The system of claim 1 wherein the learning routine further defines one or more boundary conditions for distinguishing an individual from environmental objects or other individuals.

29. The system of claim 1, wherein the personalized kinetic state models measure rates of transition between one or more states and determine the rate constants for transition into or out of each state with respect to time.

30. The system of claim 29, wherein the rate constants are described by coupled differential equations, and the learning routine comprises full or partial numerical integration of the coupled differential equations to predict transitions between states based on temporal sequence and occupancy of one or more states.

31. The system of claim 29, wherein the personalized kinetic state models include coefficient values which weigh the rates of transitions into, occupancy probabilities of and confidence intervals of entering each state, and behaviors, activities and/or position changes are predicted by prospectively comparing the actual vs. predicted occupancies of said state and the time to occupancy of said state.

32. The system of claim 1 wherein the learning routine uses heart rate and electroencephalogram characteristics indicating an individual is sleeping to evaluate probability of transition to a state of standing posture.

33. The system of claim 1 wherein the learning routine uses heart rate and electroencephalogram characteristics indicating an individual is sleep walking to evaluate the probability of transition to a state of standing posture.

34. The system of claim 1 wherein the personalized kinetic state model comprises a plurality of dynamic kinetic models for the same individual, the dynamic kinetic models applicable to specific time scales, thermodynamic energetics, or volume spaces.

35. The system of claim 34 wherein the learning routine utilizes interactions between multiple dynamic kinetic models at multiple time scales, thermodynamic energetics, or volume spaces for the individual to create multi-dimensional prediction models for the individual.

36. The system according to claim 1 wherein the notification, alert or warning is directed to one or more of deploying a safety system or advising of a necessary action to relevant personnel.

37. The system of claim 36 wherein the relevant personnel comprise one or more of law enforcement, emergency workers, or health care providers.

38. The system of claim 36 wherein the relevant personnel comprise the nearest available personnel.

39. The system of claim 1, wherein the notification, alert or warning comprises the individual's predicted state and location.

40. The system of claim 39 wherein the location comprises one or more of a room number, longitude/latitude, elevation, and triangulation information.

41. The system of claim 1 wherein the notification, alert or warning comprises one or more of audio and/or video instruction to the individual.

42. The system of claim 1 wherein the notification, alert or warning comprises a deployment of counter measures.

43. The system of claim 1 further comprising a storage device, the learning routine storing data in the storage device upon detection of an individual engaged in or predicted to be in an undesired or unsafe position, posture, behavior or activity.

44. The system of claim 43, wherein the system storage device comprises a database or electronic record comprising electronic medical records, and wherein the computer system updates work flow into the medical records programs.

45. The system of claim 1, wherein the system employs an encryption algorithm to securely record and store kinesthetic activity sensor data to limit the use of the same to personnel or officials with approved clearance thereto.

46. The system of claim 1 wherein the computer system comprises one or more computers, servers, microprocessors, electronics platforms, processing devices, mobile computing devices, or other electronic hardware, software, wireless and sensory devices.

47. A system for predicting kinesthetic outcomes from observed position, posture, behavior or activity of an individual, comprising
 a plurality of kinesthetic activity sensors each collecting one or more of audio, video, or physiological signals capturing the activity of the individual or an ambient environment of the individual;
 a computer system connected to the kinesthetic activity sensors and implementing a learning routine responsive to multi-dimensional data from the kinesthetic activity sensors reflecting behavior, habits, activities and/or positional changes of the individual and the order in which they occur in the individual, the learning routine constructing one or more personalized kinetic state models of positional states for the individual and transitions between the positional states; wherein the learning routine further develops one or more customized multi-dimensional prediction models for the individual, and uses the multi-dimensional prediction models to predict behaviors, activities and/or positional changes likely to occur in the future; and
 a notification system initiating a notification, alert or warning upon prediction of a behavior, activity or positional change associated with an unsafe or undesired outcome, and transmitting the notification, alert or warning to a recipient associated with the individual,
 wherein the learning routine defines a plurality of states, s, and characterizes each state by the amount or percent of time, t, spent therein and the degree of recurrence, r, of a certain position, posture, behavior or activity, and
 wherein the learning routine re-evaluates previously designated states and adds or subtracts states, adjusts boundary conditions, and modifies transition rates and other coefficients to create one or more dynamic personalized kinetic state models based on t, r, and total duration of observation for an individual.

48. A system for predicting kinesthetic outcomes from observed position, posture, behavior or activity of an individual, comprising
 a plurality of kinesthetic activity sensors each collecting one or more of audio, video, or physiological signals capturing the activity of the individual or an ambient environment of the individual;
 a computer system connected to the kinesthetic activity sensors and implementing a learning routine responsive to multi-dimensional data from the kinesthetic activity sensors reflecting behavior, habits, activities and/or positional changes of the individual and the order in which they occur in the individual, the learning routine constructing one or more personalized kinetic state models of positional states for the individual and transitions between the positional states; wherein the learning routine further develops one or more customized multi-dimensional prediction models for the individual, and uses the multi-dimensional prediction models to predict behaviors, activities and/or positional changes likely to occur in the future; and
 a notification system initiating a notification, alert or warning upon prediction of a behavior, activity or positional change associated with an unsafe or undesired outcome, and transmitting the notification, alert or warning to a recipient associated with the individual,
 wherein the learning routine distinguishes positional states of the individual including one or more of: sleeping, supine, sitting, getting up from a bed or chair, standing, ambulating, walking, unsteady gait, exercising, eating, transition states, and
 wherein the learning routine uses the personalized kinetic state models to calculate likelihood, hazards ratio, confidence intervals, conditional probabilities of entering a certain state given the occupancy of one or more other states within a certain temporal period or volume space, and an nth-order probability density function for the ordered sequence of states, rates of transition to and from one or more states, and feedback weighing of these factors and coefficients based on the positive and negative predictive accuracy of each model.

* * * * *